US008207328B2

(12) United States Patent
Dekany et al.

(10) Patent No.: US 8,207,328 B2
(45) Date of Patent: Jun. 26, 2012

(54) LACTOSAMINE DERIVATIVES

(75) Inventors: Gyula Dekany, Queensland (AU);
Karoly Agoston, Székesfehérvár (HU);
István Bajza, Debrecen (HU); Marie Bøjstrup, Copenhagen Ø (DK); Lars Kröger, Hamburg (DE)

(73) Assignee: Glycom Aps, Lyngby (DK)

( * ) Notice: Subject to any disclaimer, the term of this patent is extended or adjusted under 35 U.S.C. 154(b) by 725 days.

(21) Appl. No.: 12/225,094

(22) PCT Filed: Mar. 13, 2007

(86) PCT No.: PCT/DK2007/000123
§ 371 (c)(1),
(2), (4) Date: Mar. 13, 2009

(87) PCT Pub. No.: WO2007/104311
PCT Pub. Date: Sep. 20, 2007

(65) Prior Publication Data
US 2009/0234111 A1    Sep. 17, 2009

(30) Foreign Application Priority Data

Mar. 13, 2006 (DK) .................................. 2006 00355

(51) Int. Cl.
*C13K 5/00* (2006.01)
*C07H 5/04* (2006.01)
(52) U.S. Cl. .................................. 536/123.13; 536/18.7
(58) Field of Classification Search .................. 536/18.7
See application file for complete search history.

(56) References Cited

OTHER PUBLICATIONS

C-H. Wong, et al., Enzymes in Organic Synthesis: Application to the Problems of Carbohydrate Recognition (Part 2), *Angew. Chem. Int. Ed. Engl.* (1995);34:521-546.
J. Fang, et al., Chemical and Enzymatic Synthesis of Glycoconjugates 3: Synthesis of Lactosamine by Thermophilic Galactosidase Catalyzed Galactosylation on a Multigram Scale, *Tetrahedron Letters* (1998);39:919-922.
R. Kuhn, et al., Darstellung von N-Acetyl-Lactosamin (4-β-D-Galaktopyranosyl-2-desoxy-2-acetamino-D-glucopyranose) aus Lactose, *Liebigs Ann. Chem.* (1956);600:135-143 (with Abstract and English language translation thereof).
R.T. Lee, et al., A simple preparation of 2-acetamido-2-deoxy-4-0-β-D-galactopyranosyl-D-glucose and -D-mannose, *Carbohydrate Research* (1979);77:270-274.
J. Alais, et al., A convenient synthesis of N-acetyllactosamine, *Carbohydrate Research* (1981);93:164-165.
E. Lattová, et al., Synthesis of N-acetyl-lactosamine via ozonolysis of a nitro derivative, *Carbohydrate Research* (1992);235:289-293.
E. Kaji, et al., Expedient Conversion of Lactose into Versatile Derivatives of Lactosamine and β-D-Galactosyl-(1→4)-D-Mannosamine, *J. Carbohydrate Chemistry* (1995);14:791-803.
G. Kretzschmar, et al., Large Scale Synthesis of Linker-Modified Sialyl Lewis$^x$, Lewis$^x$ and N-Acetyllactosamine, *Tetrahedron* (1998);54:6341-6358.
K. Sakai, et al., Enzymatic Synthesis of N-Acetyllactosamine and N-Acetylallolactosamine by the Use of β-D-Galactosidases, *J. Carbohydrate Chemistry* (1992);11:553-565.

T. Usui, et al., A convenient synthesis of β-D-galactosyl disaccharide derivatives using the β-D-galactosidase from Bacillus circulans, *Carbohydrate Research* (1993);244:315-323.
G.F. Herrmann, et al., A New Multi-Enzyme System for a One-Pot Synthesis of Sialyl Oligosaccharides: Combined Use of β-Galactosidase and α(2,6)-Sialyltransferase Coupled with Regeneration in situ of CMP-Sialic Acid, *Tetrahedron Letters* (1993);34:3091-3094.
A.K. Sarkar, et al., Synthesis and glycan priming activity of acetylated disaccharides, *Carbohydrate Research* (2000);329:287-300.
H. Paulsen, Syntheses, Conformations and X-Ray Structure Analyses of the Saccharide Chains from the Core Regions of Glycoproteins, *Angew. Chem. Int. Ed. Engl.* (1990);29:823-839.
K. Toshima, et al., Recent Progress in O-Glycosylation Methods and Its Application to Natural Products Synthesis, *Chem. Rev.* (1993);93:1503-1531.
R.R. Schmidt, et al., Anomeric-Oxygen Activation for Glycoside Synthesis: The Trichloroacetimidate Method, *Adv. Carbohydr. Chem. Biochem.* (1994);50:21-123.
P.J. Garegg, Thioglycosides as Glycosyl Donors in Oligosaccharide Synthesis, *Adv. Carbohydr. Chem. Biochem.* (1997);52:179-205.
P.P. Deshpande, et al., Strategy in Oligosaccharide Synthesis: An Application to a Concise Total Synthesis of the KH-1(adenocarcinoma) Antigen, *J. Am. Chem. Soc.* (1998);120:1600-1614.
Y. Ichikawa, et al., Chemical-Enzymatic Synthesis and Conformational Analysis of Sialyl Lewis x and Derivatives, *J. Am. Chem. Soc.*(1992);114:9283-9298.
T. Kimura, et al., A Practical Method for the Synthesis of N-Acetyl-D-lactosamine Derivatives by the Tandem Use of Galactose Oxidase and β-Galactosidase, *Angew. Chem. Int. Ed. Engl.* (1996);35:2348-2350.
G.F. Herrmann, et al., Continuous Catalytic Synthesis of N-Acetyl-lactosamine, *Angew. Chem. Int. Ed. Engl.* (1993);32:1342-1343.
J.H. Yoon, et al., The efficient enzymatic synthesis of N-acetyl-lactosamine in an organic co-solvent, *Carbohydrate Research* (2000);327:377-383.
C.H. Wong, et al., Enzyme-Catalyzed Synthesis of N-Acetyl-lactosamine with in Situ Regeneration of Uridine 5'-Diphosphate Glucose and Uridine 5'-Diphosphate Galactose, *J. Org. Chem.* (1982);47:5416-5418.
J. Thiem, et al., Synthesis of Galactose-Terminated Oligosaccharides by Use of Galactosyltransferase, *Synthesis* (1992);141-145. T.M. Wrodnigg, et al., The Heyns Rearrangement Revisited: An Exceptionally Simple Two-Step Chemical Synthesis of D-Lactosamine from Lactulose, *Angew. Chem. Int. Ed. Engl.* (1999);38:827-828.
A. Zervosen, et al., A Novel Three-Enzyme Reaction Cycle for the Synthesis of N-Acetyllactosamine with in Situ Regeneration of Uridine 5'-Diphosphate Glucose and Uridine 5'-Diphosphate Galactose, *J. Am. Chem. Soc.* (1996);118:1836-1840.
K. Heyns, et al., Über Bildung und Darstellung von d-Glucosamin aus Fructose und Ammoniak, *Chemische Berichte* (1953);86:1453-1462 (with Abstract and English language translation thereof).
K. Heyns, et al., Ketosylamin-Umlagerung bei der Umsetzung von D-Fructose mit Pyrrolidin, *Chemische Berichte* (1968);101:2807-2814 (with Abstract and English language translation thereof).
A.E. Stütz, et al., An Exceptionally Simple Chemical Synthesis of O-Glycosylated D-Glucosamine Derivatives by Heyns Rearrangement of the Corresponding O-Glycosyl Fructoses, *Journal of Carbohydrate Chemistry* (2003);22:253-265.
R.L. Halcomb in Enzyme Catalysis in Organic Synthesis (Eds.: K. Drauz, H. Waldmann), *VHC, Weinheim* (1995) pp. 279-316.

*Primary Examiner* — Elli Peselev
(74) *Attorney, Agent, or Firm* — Harness, Dickey & Pierce, P.L.C.

(57) ABSTRACT

Lactosamine derivatives and related methods suitable for the preparation, including large-scale production, of N-acetyllactosamine, lactosamine, numerous lactosamine salts and a number of lactosamine-containing oligosaccharides are provided.

21 Claims, No Drawings

LACTOSAMINE DERIVATIVES

CROSS-REFERENCE TO RELATED APPLICATIONS

This is a National Phase Application of PCT/DK2007/000123, filed Mar. 13, 2007, and claims priority under 35 U.S.C. §119 to Denmark Patent Application No. 2006-00355 filed Mar. 13, 2006.

FIELD OF THE INVENTION

The present invention provides novel lactosamine derivatives and related methods suitable for the preparation N-acetyllactosamine, lactosamine, numerous lactosamine salts and a number of lactosamine-containing oligosaccharides. The present invention also provides new economic methods for large-scale production of N-acetyllactosamine, lactosamine and numerous lactosamine salts.

BACKGROUND OF THE INVENTION

Lactosamine is one of the most common components of natural oligosaccharides which plays essential roles in important biological events. In the structures of natural oligosaccharides and glycoconjugates, the amino group of lactosamine residues is acylated providing N-acetyllactosamine or N-lipophilic acylated lactosamine derivatives. Several glycosaminoglycan structures combine lactosamine components in N-sulfated forms which are also involved in the development of numerous human diseases.

The chemical preparation of lactosamine derivatives is rather challenging via glycosylation chemistries due to the extremely low nucleophilicity of hydroxyl groups at C-4 position of N-acetylglucosamine derivatives. The yields of procedures based upon the 4-O-galactosylation of glucosamine derivatives are always low independently from the applied glycosylation chemistries.

N-Acetyllactosamine itself has often been the major synthetic target for chemists. Thus, numerous different approaches have been described providing the targeted compound via chromatography during multi-step syntheses of protected intermediates.[1,3] In all cases, the overall yield remained low and the synthetic processes inefficient.

Enzymatic approaches for the preparation of N-acetyllactosamine using both glycosidases and glycosyltransferases has been described, which could not provide the very base of economical large-scale production processes.[2,9]

The present invention provides an excellent method for the replacement of the low yielding 4-O galactosylation of glucosamine acceptors by using lactulose as a precursor for the preparation of numerous lactosamine derivatives.

It is known from literature, that Heyns rearrangement of ketosyl amines results the formation of aldosamines in various yields[10,11]. The stereoselectivity of the reaction depends mainly on the structure of amines used for the formation of ketosyl amines.

The reaction sequence has been performed using benzyl amine and in the mixture of products only gluco isomer was present.[12]

The present invention provides novel lactosamine derivatives that can be prepared from the crude reaction mixture after the Heyns rearrangement with a highly economic way. The formed novel products could be used for the manufacture of lactosamine, N-acetyllactosamine, and various salts of lactosamine in industrial scales.

SUMMARY OF THE INVENTION

The first aspect of the present invention provides novel optionally substituted N-benzyl derivatives of lactosamine and their numerous salts.

The second aspect of the present invention provides novel methods suitable for the preparation and the use of substituted and unsubstituted N-benzyl derivatives of lactosamine and salts thereof.

The third aspect of the present invention provides novel processes for the manufacture of lactosamine, lactosamine salts and N-acetyllactosamine using novel optionally substituted N-benzyllactosamine precursors.

The fourth aspect of the present invention provides novel optionally substituted N-benzyloxycarbonyl derivatives of lactosamine.

The fifth aspect of the present invention provides methods for the preparation and the use of optionally substituted N-benzyloxycarbonyl derivatives of lactosamine such as the preparation of lactosamine, lactosamine salts and N-acetyllactosamine.

The sixth aspect of the present invention provides novel N-Dmc derivatives of lactosamine.

The seventh aspect of the present invention provides methods for the preparation and use of N-Dmc-derivatives of lactosamine such as the preparation of lactosamine, its salts and N-acetyllactosamine.

The eighth aspect of the present invention provides novel acyclic vinylogous amide derivatives of lactosamine.

The ninth aspect of the present invention provides methods for the preparation and use of acyclic vinylogous amide derivatives of lactosamine especially for the preparation of lactosamine and N-acetyllactosamine.

The tenth aspect of the present invention provides new utilities of lactosamine, its salts and N-acetyllactosamine as functional food, functional food additive, prebiotic agent, component of Infant formula and component of baby food.

The eleventh aspect of the present invention provides new utilities for lactosamine, its salts and N-acetyllactosamine as insulin secretion enhancing agent, GLP1 secretion enhancing agent and mammalian immune system enhancing agent.

The twelfth aspect of the present invention provides novel utilities to lactosamine, its salts and N-acetyllactosamine as active component of pharmaceutical compositions characterized by galectin inhibitor and antimicrobial properties.

DETAILED DESCRIPTION OF THE INVENTION

Lactosamine and its derivatives play important roles in biological systems. This simple disaccharide residue can be found in many biologically active oligosaccharides such as blood group antigens, cell surface antigens and human milk oligosaccharides. There is a significant demand for large scale and economical production of lactosamine, N-acetyllactosamine and numerous other lactosamine derivatives as building blocks or intermediates of more complex structures.

The main subject of the present invention is to provide several different novel lactosamine derivatives and methods for the preparation and use of these substances.

The first aspect of the present invention provides novel substituted and unsubstituted N-benzyl derivatives of lactosamine and their numerous salts by isolating the novel compounds characterized by General Formula 1 from Heyns re-arrangement reaction mixture. The use of benzhydrylamine, tritylamine, naphthylmethylamine in Heyns re-arrangement is also believed to be a novel feature of the present invention. These bulky substituents in the lactosamine structures occupy exclusively equatorial positions making the rearrangement itself stereoselective.

These compounds have to the best of the inventors' knowledge never been isolated and fully characterized due to isolation difficulties. The present invention represents the first case when these compounds could be isolated, characterized and used for further chemistries in their pure forms.

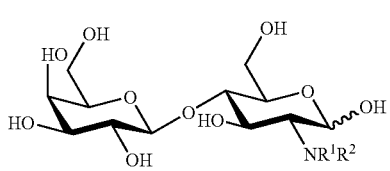

General Formula 1 wherein $R^1$ is selected from the group consisting of optionally substituted acyl and optionally substituted alkyloxycarbonyl; and $R^2$ is selected from the group consisting of optionally substituted benzyl, optionally substituted benzhydryl, optionally substituted trityl, and optionally substituted naphthylmethyl.

Definitions

In the present context, the term "alkyl" is intended to mean a linear or branched hydrocarbon group having 1 to 20 carbon atoms, such as methyl, ethyl, propyl, iso-propyl, butyl, tert-butyl, iso-butyl, pentyl, hexyl, octyl, nonyl, decyl, undecyl, dodecyl, etc.

The term "acyl" means "$C_{1-19}$—C(=O)—, $C_{1-19}$OC(=O)—".

For the purposed of this specification with claims, the term "optionally substituted" means that the group in question may either carry a substituent or may be unsubstituted.

For the purpose of this specification with claims, the term "substituted" in the definitions of $R^1$ $R^2$ and in definitions of other substituents within this specification, means that the substituent is itself substituted with a group which modifies the general chemical characteristics of the chain. Preferred substituents include but are not limited to halogen, nitro, amino, azido, oxo, hydroxyl, thiol, carboxy, carboxy ester, carboxamide, alkylamino, alkyldithio, alkylthio, alkoxy, acylamido, acyloxy, or acylthio, each of 1 to 3 carbon atoms. Such substituents can be used to modify characteristics of the molecule as a whole, such as stability, solubility, and ability to form crystals. The person skilled in the art will be aware of other suitable substituents of a similar size and charge characteristics, which could be used as alternatives in a given situation.

More generally in connection with the terms "alkyl" and "acyl" the term "optionally substituted" is intended to mean that the group in question may be substituted one or several times, preferably 1-3 times, with group(s) selected from the group consisting of hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alkanoyloxy, $C_{1-6}$-alkyl-sulphonyl, $C_{1-6}$-alkyl-sulphinyl, $C_{1-6}$-alkyl-sulphonyloxy, nitro, $C_{1-6}$-alkylthio, halogen, where any aryl and heteroaryl may be substituted as specifically described below for "optionally substituted aryl and heteroaryl", and any alkyl, alkoxy, and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidino.

Preferably, the substituents are selected from the group consisting of hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkylcarbonyl, formyl, aryl, aryloxy, arylamino, arylcarbonyl, heteroaryl, heteroarylamino, heteroaryloxy, heteroarylcarbonyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, guanidino, carbamido, $C_{1-6}$-alkyl-sulphonyl-amino, $C_{1-6}$-alkyl-sulphonyl, $C_{1-6}$-alkyl-sulphinyl, $C_{1-6}$-alkylthio, halogen, where any aryl and heteroaryl may be substituted as specifically described below for "optionally substituted aryl and heteroaryl".

Especially preferred examples are hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, and guanidino.

The second aspect of the present invention provides an absolutely new group of lactosamine compounds characterized by General Formula 2.

It is an important realization of the present invention that acyclic vinylogous reagents are able to react with N-substituted lactosamine derivatives providing structures of General Formula 2. These novel acyclic vinylogous lactosamine derivatives could often be easily separated from the multi-component Heyns re-arrangement mixture via crystallization, selective precipitation or via simple chromatography. These novel compounds can provide essential purification tool for even multi-ton-scale production methods.

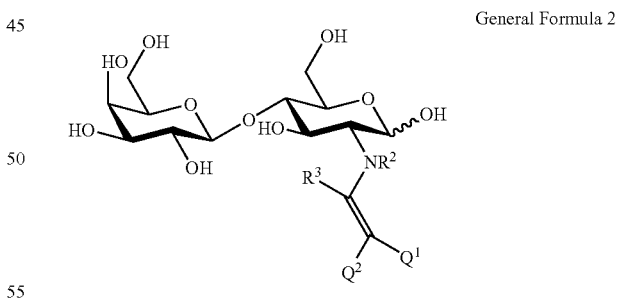

General Formula 2 wherein $R^2$ is as defined in General Formula 1, or $R^2$ is hydrogen;

$R^3$ is selected from the group consisting of optionally substituted $C_{1-6}$-alkyl, optionally substituted heteroalkyl, optionally substituted heterocyclyl, optionally substituted aryl, optionally substituted $C_{2-6}$-acyl, and hydrogen; and $Q^1$ and $Q^2$ are independently selected from the group of electron withdrawing substituents, such as CN, C=OOH, C=OOR$^4$, C=OR$^4$, C=ONH$_2$, C=ONHR$^4$, C=ONR$^4$R$^5$, optionally substituted aryl, $CF_3$, $CCl_3$, $SOR^4$, $SO_2R^4$, optionally substituted acyl; wherein $R^4$ and $R^5$ are optionally substituted alkyl, optionally substituted aryl.

In a preferred embodiment novel N-substituted lactosamine derivatives are characterized by General Formula 3:

General Formula 3

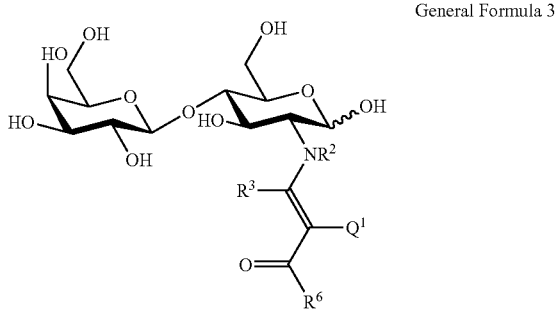

wherein $R^2$ is as defined in General Formula 1, or $R^2$ is hydrogen;

$R^3$ and $Q^1$ are as defined for General Formula 2; and $R^6$ is selected from the group consisting of $R^4$, OH, $OR^4$, $NH_2$, $NHR^4$, and $NHR^4R^5$; wherein $R^4$ and $R^5$ are as defined in General Formula 2.

In further preferred embodiment novel N-substituted lactosamine derivatives are characterized by General Formula 4:

General Formula 4

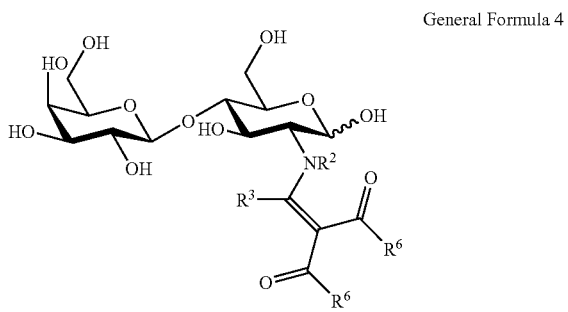

wherein $R^2$ is as defined in General Formula 1, or $R^2$ is hydrogen;

$R^3$ is as defined in General Formula 2; and $R^6$ is as defined in General Formula 3.

In a still further preferred embodiment novel N-substituted lactosamine derivatives are characterized by General Formula 5:

General Formula 5

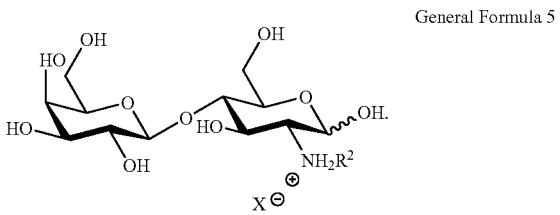

wherein $R^2$ is as defined in General Formula 1; and

X is any inorganic or organic anion known in Art.

The anion, X, can be mono- or multivalent, and may form a complex salt. Examples of anions are halides, anions of organic acids, anions of mineral acids, etc. Examples hereof are chloride ($Cl^-$), bromide ($Br^-$), iodide ($I^-$), acetate, lactate, maleate, fumerate, oxalate, sulphate, hydrogensulphate, nitrate, phosphate, hydrogenphosphate, dihydrogenphosphate, etc.

A further aspect of the present invention provides novel methods suitable for the preparation of substituted and unsubstituted N-benzyl, N-benzhydryl, N-trityl, N-naphthylmethyl derivatives of lactosamine and salts thereof.

Optionally substituted derivatives N-benzyl, optionally substituted derivatives N-benzhydryl, optionally substituted derivatives of N-trityl and optionally substituted derivatives of N-naphthylmethyl lactosamine have never been Isolated in pure form and characterized. The present invention provides a simple chromatographic separation of the titled compounds using highly basic eluents containing aqueous ammonia. The degradation of these sensitive compounds as free bases could be prevented by the presence of ammonia and further isolation by evaporation, liophylisation, selective precipitation becomes possible.

The preparation of free N-substituted lactosamine base gave direct access to numerous lactosamine salt formation either in aqueous or in anhydrous solutions using the corresponding acids.

Thus, for example, N-benzyl lactosamine could be obtained in excellent yield using Heyns rearrangement of N-benzyl lactulosyl amine. Subsequent chromatographic separation provided N-benzyl-lactosamine as a pure base. Additional salt formations with acids, such as aqueous HCl, anhydrous HCl in MeOH, sulphuric acid, etc. gave the novel N-substituted lactosamine salts in quantitative yields.

The present invention provides novel methods for the use of purified N-substituted lactosamines characterized by General Formula 5.

One of the most important applications of novel compounds of General Formula 5 is the removal of $R^2$ substitutent by hydrogenolysis or any other method known in art to produce different lactosamine salts. The reaction could be catalyzed with numerous Pd, Ni or other metal catalysts known in art at a wide range of temperature and pressure. The hydrogenolized product has excellent purity and doesn't require further purification.

N-Acylation is also an important derivatisation of novel compounds characterized by General Formula 5 providing N-acyl-lactosamine derivatives described in General Formula 1.

Typically the reaction is carried out either in aqueous or anhydrous solution with the use of an acylating agent in the presence/absence of a base. Solvents are included but not limited to acetone, methanol, water, 1,4-dioxane, DMF, tetrahydrofurane, alcohols etc and the mixtures of thereof.

The acylating agents are activated organic acids known in art. Typically acid anhydrides, like acetic anhydride, or acid halogenides like acetyl chloride used as an acylating agents. Base used for the reaction are inorganic or organic bases known in art. Typically Inorganic bases applied for the reaction are potassium carbonate, sodium carbonate or sodium hydrogencarbonate, organic bases are pyridine, triethylamine or diisopropyl ethyl amine. The reaction time for the acylation typically varies from 30 min to 24 hours depending on the structures of substrates, the set temperature and the nature of acylating agent and the base used. The products are typically obtained in high yields of 80 to 95%.

A preferred method of the present invention is suitable for the preparation of novel N-benzyl lactosamine derivatives is the carbamoylation of the free amine. Typically the reaction carried out in solution with a carbamoylation agent in the presence, or absence a base. Solvents including but not limited to acetone, methanol, water, 1,4-dioxane, DMF, tetrahydrofurane, etc and the mixtures of thereof can be used for such chemical transformation.

The carbamoylation agents are activated acyclic carbamates known in the art. Typically acyl halogenides such as benzyloxycarbonyl chloride, trichlorethyloxycarbonyl chloride, active esters of O-alkyl-substituted carbonic acid known in art could be used as acylating agents. Base catalysts applied for the acylation reaction are inorganic or organic bases known in art. Typically inorganic bases applied for the reaction are potassium carbonate, sodium carbonate or sodium hydrogencarbonate, organic bases are pyridine, triethylamine or diisopropyl ethyl amine. The reaction time for the carbamoylation typically varies from 30 min to 24 hours depending on the structures of substrates, the set temperature and the nature of carbamoylation agent and the base used. The products are typically obtained in high yields of 80 to 95%.

The present invention also provides methods for the preparation of novel N-substituted (N-benzyl, N-naphthylmethyl, N-benzhydryl, N-trityl, etc) lactosamine derivatives via the protection of the N-substituted amine with acyclic vinylogous reagents.

Typically the reaction is carried out in solution with the use of an activated vinylogous reagent in the presence, or absence a base. Solvents including but not limited to acetone, methanol, water, 1,4-dioxane, DMF, tetrahydrofurane, etc and the mixtures of thereof can be used for such chemical transformation.

Preferably, the leaving group of the applied vinylogous reagents could be alkoxy, aryloxy, alkylamino and dialkylamino groups prepared from active methylene derivatives with trialkyl orthoformate, or N,N dimethyl formamide dimethyl acetal. Base used for the reaction are inorganic or organic bases known in art. Typically inorganic bases applied for the reaction are potassium carbonate, sodium carbonate or sodium hydrogencarbonate, organic bases are pyridine, triethylamine or diisopropyl ethyl amine. The reaction time typically varies from 30 min to 24 hours depending on the structures of substrates, the set temperature and the nature of the reactive agent and the base used. The products are typically obtained in high yields of 80 to 95%.

A further aspect of the present invention provides novel processes for the preparation of lactosamine, lactosamine salts and N-acetyllactosamine and other lactosamine derivatives using novel optionally substituted N-lactosamine derivatives characterized by General Formulae 1-5.

A preferred method for the preparation of lactosamine, lactosamine salts and N-acetyllactosamine and other lactosamine derivatives is involved in a metal catalyzed hydrogenolysis of a substance of General Formula 1-5 in the presence of acid.

Solvents used for the reduction are including but not limited to methanol, ethanol, water, acetic acid, ethylacetate, etc and the mixtures of thereof can be used for such chemical transformation.

The metal used for the reaction are including but not limited to palladium, platinum or nickel in any form like palladium on carbon, platinum oxide, Raney nickel.

The acid used for the reaction can be inorganic acids, like HCl organic acids like acetic acid. The pressure applied for the reaction varied between 1 and 50 bar.

Another preferred method for the preparation of lactosamine, lactosamine salts, N-acetyllactosamine and numerous other lactosamine derivatives is Involved in a metal catalyzed hydrogenation of a substance characterized by General Formula 2-4 in the presence of acid, followed by removal of the acyclic vinylogous amide by nitrogen nucleophiles or by halogen gas. Solvents used for the reduction are including but not limited to methanol, ethanol, water, acetic acid, ethylacetate, etc and the mixtures of thereof can be used for such chemical transformation.

The metal used for the reaction are including but not limited to palladium, platinum or nickel in any form like palladium on carbon, platinum oxide, Raney nickel. The acid used for the reaction can be Inorganic acids, like HCl organic acids like acetic acid. The pressure applied for the reaction varied between 1 and 50 bar.

The removal of the acyclic vinylogous amide typically done by using aqueous or anhydrous primary amines, like ethylamine, butylamine, etc, or hydrazines, like hydrazine hydrate, hydrazine acetate etc, hydroxylamine derivatives or aqueous ammonia solution or ammonia gas in anhydrous conditions.

The present invention also provides methods using chlorine gas for the removal of acyclic vinylogous amide protecting groups providing lactosamine hydrochloride in one operational step.

One preferred embodiment of the present invention provides novel N-benzyloxycarbonyl lactosamine derivatives characterized by General Formula 6:

General Formula 6

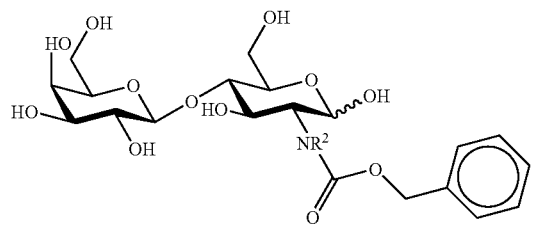

wherein $R^2$ is as defined in General Formula 1.

An additional aspect of the present invention provides methods for the preparation and the use of optionally substituted N-benzyloxycarbonyl derivatives of lactosamine of General Formula 6 such as the preparation of lactosamine, lactosamine salts and N-acetyllactosamine.

A preferred method for the preparation of optionally substituted N-benzyloxycarbonyl derivatives of lactosamine includes the N-benzyloxycarbonyl protection of the crude mixture obtained by hydrogenolysis of a Heyns rearrangement product followed by purification of the product.

Solvents used for the reaction are including but not limited to methanol, ethanol, water, acetic acid, ethylacetate, DMF, THF etc and the mixtures of thereof can be used for such chemical transformation.

The reactive agents used for the reaction are activated carbobenzyloxy (Z) derivatives, like Z—Cl, or Z-OSu.

Base used for the reaction are Inorganic or organic bases known in art. Typically inorganic bases applied for the reaction are potassium carbonate, sodium carbonate or sodium hydrogencarbonate, organic bases are pyridine, triethylamine or diisopropyl ethyl amine. The reaction time typically varies from 30 min to 24 hours depending on the structures of substrates, the set temperature and the nature of the reactive agent and the base used. The products are typically obtained in high yields of 80 to 95%.

A preferred embodiment uses the purified N-benzyl derivative of lactosamine in similar reaction conditions described above.

One of the most important preferred embodiments of the present invention is suitable for large-scale preparation of lactosamine, lactosamine salts and N-acetyllactosamine using metal catalyzed hydrogenolysis of a substance characterized by General Formula 6 in the presence of acid.

Solvents used for the reduction are including but not limited to methanol, ethanol, water, acetic acid, ethylacetate, etc and the mixtures of thereof can be used for such chemical transformation.

The metal used for the reaction are including but not limited to palladium, platinum or nickel in any form like palladium on carbon, platinum oxide, Raney nickel. The acid used for the reaction can be inorganic acids, like HCl organic acids like acetic acid. The pressure applied for the reaction varied between 1 and 50 bar.

In the case of N-acetyl lactosamine preparation, the hydrogenolysis is followed by a selective N-acetylation step carried out in water, methanol, or other suitable solvent with the treatment of acetic anhydride or acetyl chloride.

Another aspect of the present invention provides a novel N-Dmc derivative of lactosamine characterized by General Formula 7:

General Formula 7

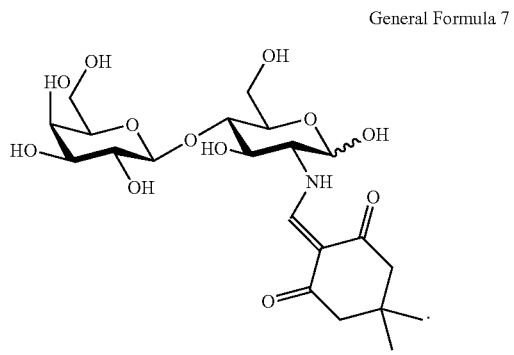

N-Dmc derivative of lactosamine has never been prepared. It is extremely important to emphasize, that the invention provides a simple method for the preparation of compounds of General formula 7 using Heyns re-arrangement followed by N-derivatisation and crystallization. This procedure could be scaled-up to provide a base of large-scale production.

A further aspect of the present invention provides methods for the preparation and use of N-Dmc-derivative of lactosamine of General Formula 7 such as the preparation of lactosamine, its salts and N-acetyllactosamine.

A preferred method for the preparation of novel N-Dmc derivative of lactosamine is the reaction of the crude reaction mixture obtained by hydrogenation of a Heyns rearrangement products with acyclic vinylogous reagent prepared by the condensation of dimedone with N,N-dimethylformamide dimethylacetal.

Typically the reaction is carried out in solution with an activated Dmc reagent (leaving groups are O-alkyl, O-aryl, N-alkyl, N,N-dialkyl) in the presence, or absence a base.

Solvents including but not limited to acetone, methanol, water, 1,4-dioxane, DMF, tetrahydrofurane, water, methanol, ethanol, etc and the mixtures of thereof can be used for such chemical transformation.

For the reagent preparation, the methylene function of dimedone is activated with trimethyl orthoformiate, or N,N dimethylformamide dimethyl-acetal.

Base used for the reaction are inorganic or organic bases known in art. Typically inorganic bases applied for the reaction are potassium carbonate, sodium carbonate or sodium hydrogencarbonate, organic bases are pyridine, triethylamine or diisopropyl ethyl amine.

The reaction time typically varies from 30 min to 24 hours depending on the structures of substrates, the set temperature and the nature of the reactive agent and the base used. The products are typically obtained in high yields of 80 to 95% without any chromatography. The solvents used for the selective precipitation are ethanol (99%-96%), or methanol.

An additional preferred method for the preparation of lactosamine, lactosamine salts and N-acetyllactosamine from novel Dmc protected lactosamine are based upon the removal of the Dmc protecting group with nitrogen nucleophiles, or with halogen gas. Solvents used for the deprotection reaction are including but not limited to methanol, ethanol, water, acetic acid, ethylacetate, etc and the mixtures of thereof.

The removal of the Dmc group is typically done by using primary amines, like ethylamine, butyl amine, etc, or hydrazines, like hydrazine hydrate, hydrazine acetate etc, aqueous ammonia solution or ammonia gas in anhydrous conditions. The Dmc protecting group can be cleaved using chlorine gas providing lactosamine hydrochloride in one operational step. The products are typically obtained by selective precipitation adding by apolar solvents like diethylether, diisopropyl ether, hexane, ethylacetate, acetone, etc in high yields of 80 to 95%, without any chromatography.

A further aspect of the present invention provides novel acyclic vinylogous amide derivatives of lactosamine characterized by General Formula 8:

General Formula 8

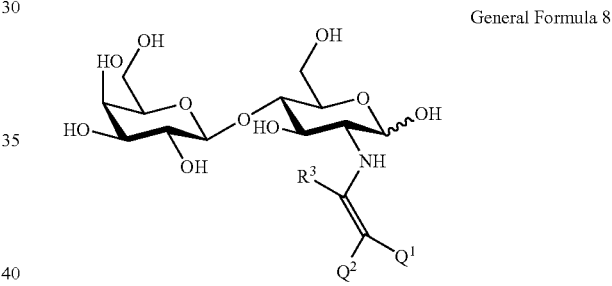

wherein $R^3$, $Q^1$ and $Q^2$ are as defined in General Formula 2.

The preparation of novel lactosamine derivatives characterized by General formula 8 could occur either by vinylogous amide protection of lactosamine itself, vinylogous reagent treatment of Heyn's re-arrangement reaction mixture or via hydrogenolysis of vinylogous compounds characterized by General Formulae 2-4 and General Formula 6.

A preferred embodiment of the present invention provides novel lactosamine derivatives characterized by General Formula 9:

General Formula 9

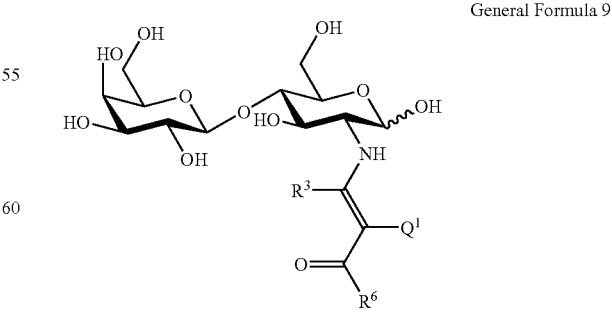

wherein $R^2$ and $Q^1$ are as defined in General Formula 2; and $R^6$ is as defined for General Formula 3.

A further preferred embodiment of the present invention provides novel lactosamine derivatives characterized by General formula 10:

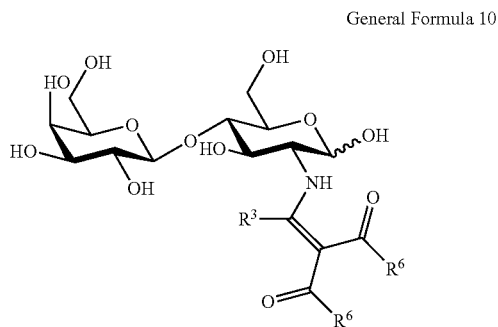

General Formula 10 wherein $R^3$ is as defined in General Formula 2; and
$R^6$ is as defined for General Formula 3.

The following aspect of the present invention provides methods for the preparation and use of acyclic vinylogous amide lactosamine derivatives of General Formula 10, especially for the preparation of lactosamine, lactosamine salts and N-acetyllactosamine.

A preferred method for the preparation of novel acyclic vinylogous amide derivatives of lactosamines of General Formula 10 involves in the treatment of free lactosamine or the Heyns rearrangement mixture itself by activated acyclic vinylogous reagents.

Typically the reaction is carried out in solution with an activated vinylogous reagent in the presence or absence of base. Solvents Including but not limited to acetone, methanol, water, 1,4-dioxane, DMF, tetrahydrofurane, alcohols, acetonitrile etc and the mixtures of thereof can be used for such chemical transformation.

For the preparation of the required vinylogous reagents, the methylene function of active methylene compounds is activated with trimethyl orthoformate, or N,N dimethyl formamide dimethyl acetal or any other reagent known by a person skilled in Art.

Base used for the reaction are inorganic or organic bases known in art. Typically Inorganic bases applied for the reaction are potassium carbonate, sodium carbonate or sodium hydrogencarbonate, organic bases are pyridine, triethylamine or diisopropyl ethyl amine.

The reaction time typically varies from 30 min to 24 hours depending on the structures of substrates, the set temperature and the nature of the reactive vinylogous agent and the base used. The products are typically obtained in high yields of 80 to 95% without any chromatography.

An additional preferred embodiment describes methods for the preparation of lactosamine, lactosamine salts and N-acetyllactosamine from novel acyclic vinylogous amide derivatives of lactosamine by the removal of the vinylogous amide protecting group with nitrogen nucleophiles, or halogen gas.

Solvents used for the reaction are including but not limited to methanol, ethanol, water, acetic acid, ethylacetate, acetonitrile etc and the mixtures of thereof can be used for such chemical transformation.

The removal of the vinylogous amide moiety is typically done by using amines, like ethylamine, butyl amine, etc, or hydrazines, like hydrazine hydrate, hydrazine acetate etc, aqueous ammonia solution or ammonia gas in anhydrous conditions. The usual work-up procedure could be based upon evaporation of the reaction mixture to dryness or based upon selective precipitation by addition of apolar solvents such as hexane, ether, dioxane, tetrahydrofuran, ethylacetate, acetonitrile, etc to the crude reaction mixture.

Chromatographic separation is not necessary for the isolation of lactosamine as a free base, and/or any lactosamine salt from the reaction mixture of the acyclic vinylogous amide deprotection reaction.

The vinylogous amide protecting moiety can also be cleaved using chlorine gas.

The products are typically obtained by selective precipitation adding by apolar solvents like diethylether, diisopropyl ether in high yields of 80 to 95%, without any chromatography.

Various Uses

The compounds defined herein and products obtainable by the methods according to the present invention are believed to have a plethora of uses within the pharmaceutical industry and uses nutritional components. A number of these envisaged uses resides in the hypothesis that the compounds described herein (e.g. lactosamine, lactosamine salts and N-acetyllactosamine) are believed to be galectin inhibitors. Hence, the present invention also relates to:

The use of lactosamine, lactosamine salts and N-acetyllactosamine as functional food, functional food additive, non-caloric functional food, functional food for elderly.

The use of lactosamine, lactosamine salts as component of infant formulas.

The use of lactosamine, lactosamine salts as component of baby foods.

The use of N-acetyllactosamine as component of infant formulas.

The use of N-acetyllactosamine as component of baby foods.

The use of lactosamine, lactosamine salts and N-acetyllactosamine as feed material.

The use of lactosamine and lactosamine hydrochloride as prebiotic agent.

The use of N-acetyllactosamine as a prebiotic agent.

The use of lactosamine and lactosamine salts as insulin secretion enhancing agent.

The use of N-acetyllactosamine as insulin secretion enhancing agent.

The use of lactosamine and lactosamine salts as GLP1 secretion enhancing agent.

The use of N-acetyllactosamine as GLP1 secretion enhancing agent.

The use of lactosamine and lactosamine salts as immune system enhancing agent.

The use of N-acetyllactosamine as immune system enhancing agent.

The use of lactosamine and lactosamine salts as an active antimicrobial agent of pharmaceutical compositions.

The use of N-acetyllactosamine as an active antimicrobial agent of pharmaceutical compositions.

The use of lactosamine and lactosamine salts as galectin inhibitors of pharmaceutical compositions.

The use of N-acetyllactosamine as galectin Inhibitor of pharmaceutical compositions.

References 1. a) H. Paulsen, *Angew. Chem. Int. Ed. Engl* 1990, 29, 823-938; b) K. Toshima, K. Tatsuta, *Chem. Rev. Ed. Engl.* 1993, 93, 1503-1531; c) R. R. Schmidt, W. Kinzy, *Adv. Carbohydr. Chem. Biochem.* 1994, 50, 21-123; d) P. J. Garegg, *Adv. Carbohydr. Chem. Biochem.* 1997, 52, 179-266; e) P. P. Deshpande, H. M. Kim, A. Zatorski, T.-K. Park, G. Ragupathi, P. O. Livingston, D. Live, S. J. Danishefsky, *J.*

Am. Chem. Soc. 1998, 120, 1600-1614; f) A. K. Sakar, J. R. Brown, J. D. Esko, *Carbohydr. Res.,* 2000, 329, 287-300.
2. a) C.-H. Wong, R. L. Halcomb, Y. Ichikawa, *Angew. Chem.* 1995, 107, 569-593; *Angew. Chem. Int. Ed. Engl.* 1995, 34, 521-546, and references therein; b) R. L. Halcomb in *Enzyme Catalysis in Organic Synthesis* (Eds.: K. Drauz, H. Waldmann), VCH, Weinheim, 1995, pp. 279-315.
3. a) R. Kuhn, W. Kirschenlohr, *Liebigs Ann. Chem.* 1956, 600, 135-143; b) R. T. Lee, Y. C. Lee, *Carbohydr. Res.* 1979, 77, 270-274; c) J. Alais, A. Veyrieres, *Carbohydr. Res.* 1981, 93, 164-165; d) E. Lattova, L. Petrus, *Carbohydr. Res.* 1992, 235, 289-293; e) E. Kaji, F. W. Lichtenthaler, *J. Carbohydr. Chem.* 1995, 14, 791-803; f) G. Kretschmar, W. Stahl, *Tetrahedron* 1998, 54, 6341-6358.
4. a) K. Sakai, R. Katsumi, H. Ohi, T. Usul, Y. Ishido, *J. Carbohydr. Chem.* 1992, 11, 553-565; b) T. Usul, S. Kubota, H. Ohi, *Carbohydr. Res.* 1993, 244, 315-323; c) G. F. Hermann, Y. Ichikawa, C. Wandrey, F. C. A. Gaeta, J. C. Palson, C.-H. Wong, *Tetrahedron Lett.* 1993, 34, 3091-3094; d) J. Fang, W. Xie, J. Li, P. G. Wang, *Tetrahedron Lett.* 1998, 39, 919-922.
5. T. Kimura, S. Takayama, H. Huang, C.-H. Wong, *Angew. Chem. Int. Ed. Engl.* 1996, 35, 2348-2350.
6. G. F. Hermann, U. Kragl, C. Wandrey, *Angew. Chem. Int. Ed. Engl.* 1993, 32, 1342-1343.
7. J. H. Yoon, J. S. Rhee, *J. Carbohydr. Chem.,* 2000, 327, 377-383.
8. a) C.-H. Wong, S. L. Haynie, G. M. Whitesides, *J. Org. Chem.,* 1982, 47, 5416-5418; b) J. Thlem, T. Wiemann, *Synthesis,* 1992, 141-145; c) Y. Ichikawa, Y.-C. Lin, D. P. Dumas, G.-J. Shen, E. Garcia-Junceda, M. A. Williams, R. Bayer, C. Ketcham, L. E. Walker, J. C. Paulson, C.-H. Wong, *J. Am. Chem. Soc.,* 1992, 114, 9283-9298.
9. A. Zervosen, L. Elling, *J. Am. Chem. Soc.* 1996, 118, 1836-1840.
10. K. Heyns, K.-H. Meinecke, *Chem. Ber.,* 1953, 86, 1453-1462.
11. K. Heyns, K.-W. Pflughaupt, D. Müller, *Chem. Ber.,* 1968 101, 2807-2814.
12. T. M. Wrodnigg, A. E. Stutz, *Angew. Chem. Int. Ed. Engl.* 1999, 38, 827-828.

EXAMPLES

General Procedure for the Preparation of Optionally Substituted Malonic-Acid Diamides:

1 mmol malonic-acid dimethylester and 2 mmol alkylamine mixed in round bottom flask and the mixture stirred until the starting compounds completely reacted. The reaction time varied between 30 min to 24 h and the temperature between r.t up to reflux temperature. When the reaction finished the product isolated as a white solid/crystal.

The yields were from 80% up to quantitative.

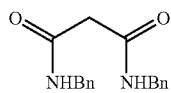

6 g malonic-acid dimethylester and 10 g benzylamine mixed in round bottom flask and the mixture stirred for 20 min at 110° C. When the reaction finished the product isolated as a white crystal (12 g).

1H NMR. (CDCl$_3$) δ: 7.77 (bs, 2 H, NH), 7.25 (m, 10 H, aromatic), 4.35 and 4.32 (s, 4 H, 2x—CH$_2$Ph), 3.19 (s, 2 H, COCH$_2$CO).

13C NMR (CDCl$_3$) δ: 167.69 (2×CO), 137.99, 128.90, 127.86, 127.86, 127.70 and 127.70 (aromatic), 43.76, 43.76 and 43.13 (2x—CH$_2$Ph and COCH$_2$CO).

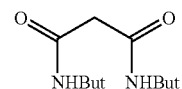

13.2 g malonic-acid dimethylester and 21.9 g butylamine mixed in round bottom flask and the mixture stirred for 2 h at 85° C. When the reaction finished the product isolated as a white crystal (29 g).

1H NMR. (CDCl$_3$) δ: 7.56 (bs, 2 H, NH), 3.18 (m, 6 H, COCH$_2$CO and 2 But), 1.38 (m, 8 H, But), 0.88 (t, 6 H, 2x—CH$_3$).

13C NMR (CDCl$_3$) δ: 167.56 (2×CO), 43.00 (COCH$_2$CO), 39.24, 31.20, 19.95 and 13.61 (Butyl).

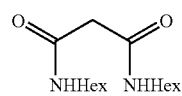

13.2 g malonic-acid dimethylester and 25.2 g hexylamine mixed in round bottom flask and the mixture stirred for 3 h at 70° C. When the reaction finished the product isolated as a white crystal (31 g).

1H NMR. (CDCl$_3$) δ: 7.51 (bs, 2 H, NH), 3.18 (m, 6 H COCH$_2$CO and 2 Hexyl), 1.48 (m, 4 H, Hexyl), 1.24 (m, 12 H, Hex), 0.83 (m, 6 H, 2x—CH$_3$).

13C NMR (CDCl$_3$) δ: 167.84 (2×CO), 43.9 (COCH$_2$CO), 39.88, 31.66, 29.44, 26.79, 22.75 and 14.21 (Hexyl).

General Procedure for the Preparation of Alkoxymethylinated and Dialkylaminomethylinated Malonic-Acid Derivatives:

1 mmol malonic-acid derivative dissolved in anhydrous organic solvent and dimethylformamide-dimethylacetal or trimethyl orthoformiate added to the mixture and stirred until the product formed. Solvents including but not limited to DCM, Toluene, Chloroform, MeCN, Aceton, EtOAc, dioxane, DMF, THF, etc and the mixtures of thereof can be used for such chemical transformation. The temperature of the reaction varied between −10° C. up to reflux temperature of the reagent. The reaction time typically varied from 10 min to 2 d depending on the structures, the set temperature, and the nature of the reactive agent. The products are isolated in high yields from 75% up to 90%.

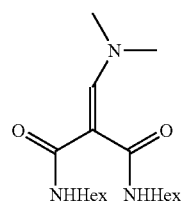

To a solution of malonic-acid dihexylamide (500 mg) in the mixture of DCM (5 mL), toluene (2 mL) and MeCN (5 mL), N,N dimethylformamide-dimethylacetal (250 μL) added slowly. Then the mixture heated up to 50° C. and stirred for 5 h. The product isolated after concentration the mixture followed by crystallization (250 mg).

1H NMR. (CDCl₃) δ: 7.44 (s, 1 H, —CH═), 7.29 and 6.54 (2 bs, each 1 H, 2×NH), 3.25 (m, 4 H, Hexyl), 2.90 (s, 6 H, 2×—NCH₃), 1.50 (m, 4 H, Hexyl), 1.25 (m, 12 H, Hex), 0.85 (m, 6 H, 2×—CH₃).

13C NMR (CDCl₃) δ: 169.46 and 167.74 (2×CO), 150.69 (—HN—CH═), 98.09 (C qvat.), 43.57 and 39.94 (2×—NCH₃), 39.83, 39.77, 31.78, 31.73, 29.95, 29.89, 26.96, 26.82, 22.80, 22.78, 14.27 and 14.24 (Hexyl).

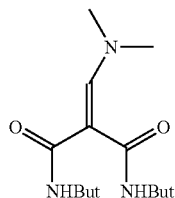

To a solution of malonic-acid dibutylamide (500 mg) in DCM (5 mL), N,N dimethylformamide-dimethylacetal (310 μL) added slowly. Then the mixture stirred at r.t. for 2 d. The product isolated after concentration the mixture followed by crystallization (310 mg).

1H NMR. (CDCl₃) δ: 7.32 and 7.10 (2 bs, each 1 H, 2×NH), 7.30 (s, 1 H, —CH═), 3.22 and 3.12 (2 m, each 2 H, 2×But), 2.81 (s, 6 H, 2×—NCH₃), 1.40 and 1.25 (2 m, each 4 H, But), 0.81 (m, 6 H, 2×—CH₃).

13C NMR (CDCl₃) δ: 169.38 and 167.89 (2×CO), 150.53 (—HN—CH═), 97.50 (C qvat.), 43.42 and 43.42 (2×—NCH₃), 39.63, 39.37, 32.01, 31.99, 20.54, 20.37, 13.97 and 13.89 (Butyl).

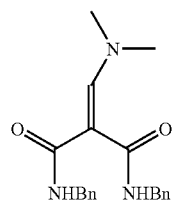

To a solution of malonic-acid dibenzylamide (500 mg) in the mixture of DCM (5 mL), toluene (2 mL) and MeCN (2 mL), N,N dimethylformamide-dimethylacetal (240 μL) added slowly. Then the mixture stirred at r.t. for 2 d. The product Isolated after concentration the mixture followed by crystallization (320 mg).

1H NMR. (CDCl₃) δ: 8.00 and 7.80 (2 bs, each 1 H, 2×NH), 7.44 (s, 1 H, —CH═), 7.25 (m, 10 H, aromatic), 4.49 and 4.43 (2 m, each 2 H, 2×—CH₂Ph), 2.73 (bs, 6 H, 2×—NCH₃).

13C NMR (CDCl₃) δ: 169.12 and 167.92 (2×CO), 151.53 (—HN—CH═), 97.02 (C qvat.), 43.78, 43.78, 43.60 and 62.62 (2×—CH₂Ph and 2×—NCH₃).

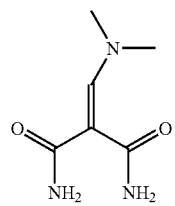

To a solution of malonic-acid diamide (1 g) in DMF (15 mL), N,N dimethylformamide-dimethylacetal (1.4 g) added slowly. Then the mixture heated up to 50° C. and stirred for 3 h. The product isolated after concentration the mixture followed by crystallization (410 mg).

1H NMR. (DMSO d6) δ: 7.45 and 7.02 (each bs, 4 H, 2×—NH₂), 7.40 (s, 1 H, —CH═), 2.94 and 2.89 (2×s, each 3 H, 2×—NCH₃).

13C NMR (DMSO d6) δ: 169.16 and 169.15 (2×CO), 151.08 (—HN—CH═), 96.37 (C qvat.), 43.07 and 42.95 (2×NCH₃).

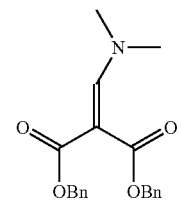

To a solution of dibenzyl malonate (2 g) in DMF (10 mL), N,N dimethylformamide-dimethylacetal (904 mg) added slowly. Then the mixture heated up to 110° C. and stirred for 30 min. The product isolated after concentration the mixture followed by crystallization (910 mg).

1H NMR. (CDCl₃) δ: 7.60 (s, 1 H, —CH═), 7.30 (m, 10 H, aromatic), 5.22 (s, 4 H, 2×—CH₂Ph), 2.80 (bs, 6 H, 2×—NCH₃).

13C NMR (CDCl₃) δ: 167.41 (2×CO), 154.70 (—HN—CH═), 92.38 (C qvat.), 66.72 and 65.91 (2×—CH₂Ph and 2×—NCH₃).

General Procedure for the Preparation of Alkoxymethylinated and Dialkylaminomethylinated 1,3-cyclohexenedione Derivatives:

1 mmol 1,3-cyclohexenedione derivative dissolved in anhydrous organic solvent and dimethylformamide-dimethylacetal or trimethyl orthoformiate added to the mixture and stirred until the product formed.

Solvents including but not limited to DCM, Toluene, Chloroform, MeCN, Aceton, EtOAc, dioxane, DMF, THF, etc and the mixtures of thereof can be used for such chemical transformation. The temperature of the reaction varied between −10° C. up to reflux temperature of the reagent. The reaction time typically varied from 10 min to 2 d depending on the structures, the set temperature, and the nature of the reactive agent. The products are Isolated in high yields from 75% up to 90%.

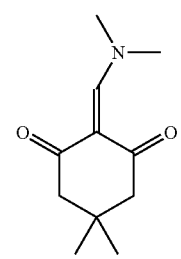

Dimedone (10 g) dissolved in CHCl₃ (60 mL) and the mixture cooled to 0° C. N,N dimethylformamide dimethylacetal (9.5 mL) in CHCl₃ (20 mL) added to the mixture slowly. Then the mixture heated up to reflux for 30 min. The product was isolated by concentrating the mixture followed by crystallization from EtOAc:Hexane (1:10, 50 mL) yielding 12.8 g yellow crystal.

1H NMR. (DMSO d6) δ: 8.01 (s, 1 H, —CH=), 3.40 and 3.18 (2×s, each 3 H, 2×NCH$_3$), 2.36 (s, 4 H, 2×CH$_2$), 1.08 (s, 6 H, 2×CH$_3$).

13C NMR (DMSO d6) δ: 195.71 and 195.70 (2×CO), 161.92 (—HN—CH=), 108.28 (C qvat.), 52.34 (2×CH$_2$), 48.44 and 44.93 (2×NCH$_3$), 31.14 and 31.05 (2×CH$_3$), 28.66 C—(CH$_3$)$_2$).

General Procedure for the Preparation of Acyclic Vinylogous Amide Derivatives of Lactosamine:

The reaction typically carried out in solution by treating lactosamine with an activated vinylogous amide reagent in the presence or absence a base. The starting lactosamine can be pure substance or mixture after Heyns rearrangement reaction. Solvents including but not limited to acetone, methanol, ethanol, water, dioxane, THF, DMF, alcohols, MeCN, and the mixtures of thereof can be used for such chemical transformation. The methylene group of the vinylogous amide reagent is activated with trimethyl orthoformate, or N,N dimethylamide dimethylacetal. Base used for the reaction are inorganic bases (like: K$_2$CO$_3$, Na$_2$CO$_3$, NaHCO$_3$, etc) or organic bases (like pyridine, triethylamine, Hunig's base, etc.). The temperature of the reaction varied between −10° C. up to reflux temperature of the solvents. The reaction time typically varied from 10 min to 2 d depending on the structures, the set temperature, and the nature of the reactive agent. The products are Isolated in high yields from 75% up to 90%.

For analytical purposes the products could have been acetylated In pyridine and Ac$_2$O.

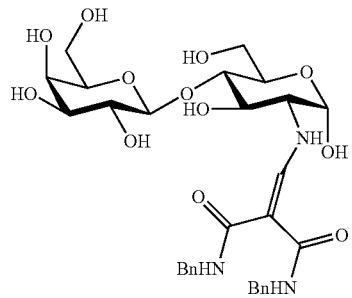

Lactosamine (500 mg) dissolved in MeOH (5 mL), and TEA (430 μL) added. Activated malonicacid dibenzylamide (500 mg) added to the mixture and stirred for 2 h. Then concentrated and the product isolated by column chromatography.

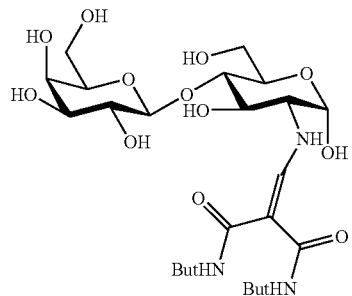

Lactosamine (500 mg) dissolved in MeOH (5 mL), and TEA (430 μL) added. Activated malonicacid dibutylamide (500 mg) added to the mixture and stirred for 2 h. Then concentrated and the product isolated by column chromatography.

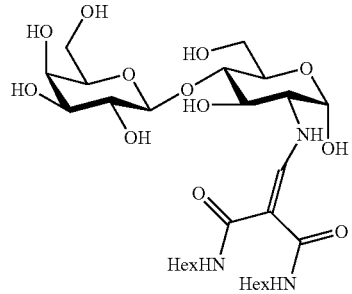

Lactosamine (500 mg) dissolved in MeOH (5 mL), and TEA (430 μL) added. Activated malonicacid dihexylamide (500 mg) added to the mixture and stirred for 2 h. Then concentrated and the product isolated by column chromatography.

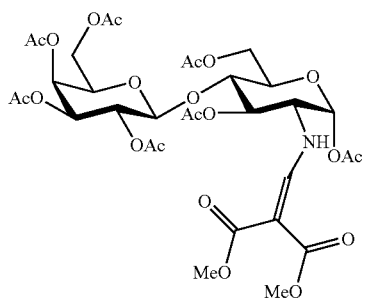

Crude mixture of Heyns rearrangement reaction (530 mg) dissolved in MeOH (5 mL), and TEA (430 μL) added. Methoxymethylenemalonic acid dimethyl ester (324 mg) added to the mixture and stirred for 2 h. Then concentrated and the product isolated by column chromatography. For analysis: compound (20 mg) dissolved in pyridine (2 mL) then Ac$_2$O (1 mL) added and stirred for 12 h. The mixture concentrated and chromatographed affording the fully acetylated product.

1H NMR. (CDCl$_3$) δ: 9.09 (dd, 1 H, J$_{NH,HC}$=13.45 Hz, J$_{NH,2}$ 9.85 Hz, NH), 7.92 (d, 1 H, —CH=), 6.18 (d, 1 H, J$_{1,2}$ 3.70 Hz, H-1), 5.35 (m, 2 H, H-3 and H-4'), 5.12 (dd, 1 H, J$_{1',2'}$ 7.83 Hz, J$_{2',3'}$ 10.34 Hz, H-2'), 4.97 (dd, 1 H, H-3'), 4.49 (d, 1 H, J$_{1,2}$ 7.85 Hz, H-1), 3.94 (m, 1 H, H-4), 3.78 and 3.72 (2×s, each 3 H, 2×OCH$_3$), 3.54 (m, 1 H, H-2), 2.26, 2.17, 2.12, 2.08, 2.05, 2.05 and 1.97 (7×s, each 3 H, 7×OAc).

13C NMR (CDCl$_3$) δ: 170.25, 170.14, 170.04, 170.04, 169.99, 169.38, 168.99, 168.7 and 165.08 (9×CO), 158.55 (—HN—CH=), 100.98 (C-1'), 91.93 (C qvat.), 90.18 (C-1), 75.19 (C-5), 70.19 (C-5'), 70.55 (C-4), 70.54 (C-3'), 70.51 (C-3), 68.92 (C-2') 66.38 (C-4'), 61.40, 60.95 and 60.56 (C-2, C-6 and C-6') 51.41 and 51.34 (2×OCH$_3$), 20.76, 20.73, 20.59, 20.58, 20.57, 20.57 and 20.43 (7×OAc).

General Procedure for the Preparation of (2-methylidinyl 1,3-cyclohexenedione Derivatives of Lactosamine:

The reaction typically carried out in solution with an activated vinylogous amide reagent in the presence or absence a base. The starting lactosamine can be clean product or mixture after Heyns rearrangement reaction. Solvents including but not limited to acetone, methanol, ethanol, water, dioxane, THF, DMF, alcohols, MeCN, and the mixtures of thereof can be used for such chemical transformation. The methylene group of the 1,3-cyclohexenedione derivative is activated with trimethyl orthoformate, or N,N dimethylamide dimethylacetal. Base used for the reaction are inorganic bases (like: $K_2CO_3$, $Na_2CO_3$, $NaHCO_3$, etc) or organic bases (like pyridine, triethylamine, Hunig's base, etc.). The temperature of the reaction varied between −10° C. up to reflux temperature of the solvents. The reaction time typically varied from 10 min to 2 d depending on the structures, the set temperature, and the nature of the reactive agent. The products are isolated in high yields from 75% up to 90%.

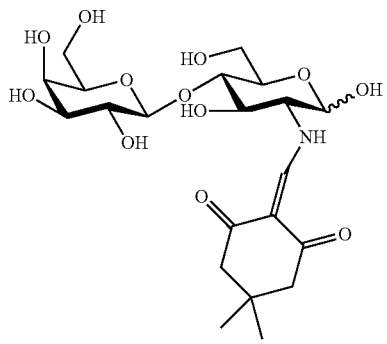

Lactosamine (8 g) dissolved in MeOH (30 mL) followed by the addition of TEA (3 mL). Then dialkylaminomethylinated-dimedon derivative (4.16 g) added in MeOH (5 mL) and the mixture stirred for 3 h. When TLC showed complete conversion the mixture concentrated and the product isolated by crystallization from EtOH affording 2.6 g white crystal.

1H NMR. ($D_2O$) δ: 8.02 (s, 1 H, —CH=α), 7.99 (s, 1 H, —CH=β), 5.17 (d, 1 H, $J_{1,2}$ 3.60 Hz, H-1α), 4.78 (d, 1 H, $J_{1,2}$ 8.16 Hz, H-1β), 3.43 (m, 1 H, H-2α), 3.34 (m, 1 H, H-2'), 3.11 (m, 1 H, H-2β), 2.24 (m, 2×$CH_2$), 0.84 and 0.83 (2×s, each 3 H, 2×—$CH_3$).

13C NMR ($D_2O$) δ: 202.42 and 201.22 (2×CO), 159.70 (—HN—CH=), 107.76 (C quat.), 102.98 (C-1'), 93.73 (C-11), 90.56 (C-1α), 77.82, 75.44, 72.57, 71.05, 70.57, 69.72 68.64, 63.93, 61.15 and 57.47 (C-2, 3, 4, 5, 6, C-2', 3', 4', 5', 6', all α), 50.45 and 50.09 (2×—$CH_2$), 27.38 and 27.38 (2×—$CH_3$).

General Procedure for the Preparation of Lactosamine Via the Use of Acyclic Vinilogous Amide Derivatives of Lactosamine:

The reaction typically carried out in solution, using amines, hydrazines or ammonia.

Solvents including but not limited to acetone, methanol, ethanol, water, dioxane, DMSO, THF, DMF, alcohols, MeCN, and the mixtures of thereof can be used for such chemical transformation. Amines like ethylamine, butylamine, benzylamine etc. hydrazines, like hydrazine acetate, hydrazine hydrate etc. or ammonia as aqueous ammonia, or anhydrous ammonia in solvent (like: methanol, dioxane, etc), or ammonia gas have been used to cleave the vinylogous amide protecting group. Products are typically obtained by selective precipitation adding apolar solvents like dietylether, diisopropyl ether, acetone ethanol, isopropanol etc in high yields of 80% to 95%, without any chromatography.

Acyclic vinylogous amide derivatives of lactosamine (200 mg) dissolved in DMSO (1 mL) and benzylamine (200 mg) added to the mixture and stirred at r.t. for 1 h. The product was isolated by precipitation with diethyl ether (20 mL).

Acyclic vinylogous amide derivatives of lactosamine (200 mg) dissolved in MeOH (10 mL) and ammonia gas bubbled through the solution for 1 h. The product was isolated by precipitation with diethyl ether (20 mL).

Acyclic vinylogous amide derivatives of lactosamine (500 mg) dissolved in MeOH (25 mL) and ammonia gas bubbled through the solution for 2 h. The product was isolated by precipitation with diethyl ether (50 mL).

Acyclic vinylogous amide derivatives of lactosamine (12 g) added to an ammonia solution in MeOH (420 mL, 8 m/m %) and the mixture stirred for 3 h. The product was isolated by precipitation with diethyl ether (900 mL).

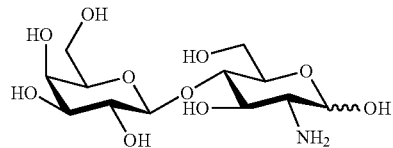

1H NMR. ($D_2O$) δ: 5.23 (d, 1 H, $J_{1,2}$ 3.10 Hz, H-1α), 4.75 (d, 1 H, $J_{1,2}$ 8.43 Hz, H-1β), 4.25 (d, 1 H, $J_{1',2'}$ 7.25 Hz, H-1'α and β) 3.34 (m, 1 H, H-2'α and β), 3.14 (dd, 1 H, H-2α), 2.83 (m, 1 H, H-2β).

13C NMR ($D_2O$) δ: 103.13 (C-1'β), 103.08 (C-1'α), 92.67 (C-1α), 88.99 (C-1β), 78.08, 75.51, 72.54, 71.05, 70.38, 68.62 68.45, 61.23, 59.74 and 54.13 (C-2, 3, 4, 5, 6, C-2', 3', 4', 5', 6', all α).

General Procedure for the Preparation of Lactosamine Via the Use of (2-methylidinyl 1,3-cyclohexenedione Derivatives of Lactosamine:

The reaction typically carried out in solution, using amines, hydrazines or ammonia.

Solvents including but not limited to acetone, methanol, ethanol, water, dioxane, DMSO, THF, DMF, alcohols, MeCN, and the mixtures of thereof can be used for such chemical transformation. Amines like ethylamine, butylamine, benzylamine etc. hydrazines, like hydrazine acetate, hydrazine hydrate etc. or ammonia as aqueous ammonia, or anhydrous ammonia in solvent (like: methanol, dioxane, etc), or ammonia gas have been used to cleave the vinylogous amide protecting group. Products are typically obtained by selective precipitation adding apolar solvents like dietylether, diisopropyl ether, acetone ethanol, isopropanol etc in high yields of 80% to 95%, without any chromatography.

(2-methylinidyl) 1,3-cyclohexenedione derivative of lactosamine (200 mg) dissolved in DMF (1 mL) and benzylamine (1 mL) added to the mixture and stirred at r.t. for 2 h. The product was isolated by precipitation with acetone (10 mL).

(2-methylinidyl) 1,3-cyclohexenedione derivative of lactosamine (100 mg) dissolved in ethanol-methanol mixture (10 mL, 1 mL respectively) and ammonia gas bubbled through the solution for 45 min. The product was isolated by precipitation with diethyl ether (5 mL).

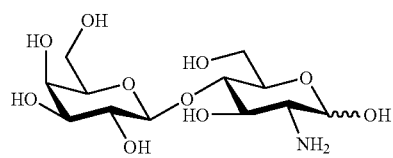

NMR Data: See previous experiment.

General Preparation of Salts of Lactosamine and Lactosamine Derivatives:

The formation of salts of lactosamine and lactosamine derivatives typically carried out in solution from the free amine form of lactosamine/derivative using inorganic or organic acids or salts. Solvents including but not limited to acetone, methanol, ethanol, water, dioxane, DMSO, THF, DMF, alcohols, MeCN, and the mixtures of thereof can be used for such chemical transformation. Inorganic acids are including nut not limited to HCl, $H_2SO_4$, $HNO_3$, $H_3PO_4$, etc in concentrated or diluted in water or any other solvents such as methanol, ethanol, dioxan, etc. The salts of these acids can be used as well. Organic acids are including but not limited to formic acid, acetic acid, oxalic acid etc and salts of these. Products are typically obtained by selective precipitation adding apolar solvents like dietylether, diisopropyl ether, acetone ethanol, isopropanol etc in high yields of 80% to 95%, or by crystallization in high yield of 80% to 95% without any chromatography.

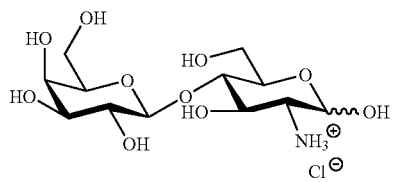

Lactosamine (200 mg) was dissolved in MeOH (3 mL), and the mixture cooled to 0° C. Then HCl in MeOH (430 µL, 1.4 mmol/mL) added to the mixture and stirred for 10 min. The product was isolated by adding EtOH (3 mL), and acetone (20 mL) yielding 120 mg white powder.

1H NMR. ($D_2O$) δ: 5.23 (d, 1 H, $J_{1,2}$ 3.10 Hz, H-1α), 4.75 (d, 1 H, $J_{1,2}$ 8.43 Hz, H-1α), 4.25 (d, 1 H, $J_{1',2'}$ 7.25 Hz, H-1'α and β) 3.34 (m, 1 H, H-2'α and β), 3.14 (dd, 1 H, H-2α), 2.83 (m, 1 H, H-2β).

13C NMR ($D_2O$) δ: 103.13 (C-1'β), 103.08 (C-1'α), 92.67 (C-1α), 88.99 (C-1β), 78.08, 75.51, 72.54, 71.05, 70.38, 68.62 68.45, 61.23, 59.74 and 54.13 (C-2, 3, 4, 5, 6, C-2', 3', 4', 5', 6', all α).

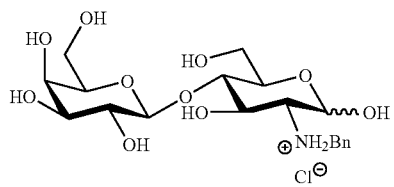

N benzyl-lactosamine (200 mg) isolated by column chromatography after Heyns rearrangement reaction was dissolved in MeOH (5 mL), and the mixture cooled to 0° C. Then HCl in MeOH (400 µL, 1.4 mmol/mL) added to the mixture and stirred for 10 min. The product was isolated by adding EtOH (2 mL), and acetone (20 mL) yielding 100 mg white powder.

1H NMR. ($D_2O$) δ: 7.30 (m, 5 H, aromatic), 5.33 (d, 1 H, $J_{1,2}$ 3.57 Hz, H-1α), 4.90 (d, 1 H, $J_{1,2}$ 8.40 Hz, H-1β), 4.23 (d, 1 H, $J_{1',2'}$ 7.69 Hz, H-1'α), 4.20 (d, 1 H, $J_{1,2}$ 7.43 Hz, H-1'β), 3.36 and 3.33 (m, 2 H, H-2'α and β), 3.10 (dd, 1 H, H-2α), 2.83 (m, 1 H, H-2β).

General Procedure for the Preparation of N-benzyloxycarbonyl Derivatives of Lactosamine:

The reaction typically carried out in solution, using clean lactosamine-lactosamine derivatives, or crude reaction mixtures after the Heyns rearrangement.

Solvents including but not limited to acetone, methanol, ethanol, water, dioxane, DMSO, THF, DMF, alcohols, MeCN, and the mixtures of thereof can be used for such chemical transformation. The reactive agents used for this reaction are activated carbobenzyloxy (Z) derivatives like Z-Cl, Z-OSu. Base used for the reaction are Inorganic bases (like: $K_2CO_3$, $Na_2CO_3$, $NaHCO_3$, etc) or organic bases (like pyridine, triethylamine, Hunig's base, etc.). The temperature of the reaction varied between −10° C. up to reflux temperature of the solvents. The reaction time typically varied from 30 min to 1 d depending on the structures, the set temperature, and the nature of the reactive agent. The products are isolated in high yields from 80% up to 95%.

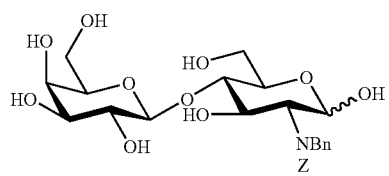

N-benzyl lactosamine (1 g, purified by column chromatography of the mixture after Heyns rearrangement) dissolved in MeOH (20 mL) and $K_2CO_3$ (500 mg) added to the mixture. Z-Cl added to a solution at 0° C. and stirred for 30 min, then concentrated. The solid residue washed with tert-butylmethylether (50 mL) to remove apolar impurities. The product obtained by washing the powder with EtOH/Acetone (70 mL, 1:1). The washings collected and concentrated.

1H NMR. ($D_2O$) δ: 7.20 (m, 10 H, aromatic), 4.38 (d, 1 H, $J_{1,2}$ 7.46 Hz, H-1'α and β), 4.27 (d, 1 H, $J_{1,2}$ 2.70 Hz, H-1α), 4.23 (d, 1 H, $J_{1,2}$ 7.02 Hz, H-1β), 3.43 (m, 1 H, H-2'α and β), 23.35 (m, 1 H, H-2α and β).

13C NMR ($D_2O$) δ: 146.13 (CO), 94.86 and 94.08 (C-1 and C-1'α), 76.69, 75.06, 74.34, 73.00, 72.59, 71.95, 71.05, 69.01, 66.00, 61.71, 61.03 and 54.55 (C-2, 3, 4, 5, 6, C-2', 3', 4', 5', 6', and 2×—$CH_2$ all α).

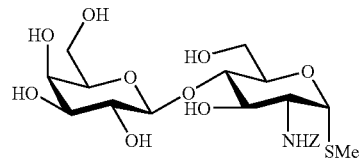

Methyl 1-deoxy-1-thio α D lactosamine (150 mg, see NMR data below) and $NaHCO_3$ (170 mg) dissolved in the mixture of water (2 mL) and MeCN (1 mL). The mixture cooled to 0° C. and Z-Cl (170 µL) added in MeCN (1 mL) and the mixture stirred for 1 h at r.t. The mixture concentrated and the residue purified by column chromatography affording 100 mg product.

1H NMR. ($CD_3OD$) δ: 7.36 (m, 5 H, aromatic), 5.36 (d, 1 H, $J_{1,2}$ 5.36 Hz, H-1), 4.38 (d, 1 H, $J_{1',2'}$ 7.16 Hz, H-2), 3.88 (m, 1 H, H-2), 3.54 (m, 1 H, H-2'), 2.05 (s, 3 H, SMe).

13C NMR ($CD_3OD$) δ: 157.37 (CO), 103.94 (C-1'), 85.38 (C-1), 80.28, 75.90, 73.58, 71.40, 69.96, 69.07 and 66.37

(C-2, C-3, C-4, C-5, C-3', C-4' and C-5'), 61.29 and 60.68 (C-6 and C-6'), 55.71 (C-2), 12.09 (SMe).

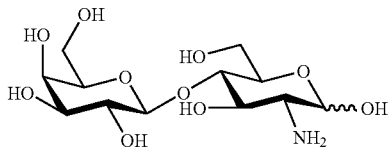

1H NMR. (D$_2$O) δ: 5.08 (d, 1 H, J$_{1,2}$ 5.20 Hz, H-1), 4.27 (d, 1 H, J$_{1',2'}$ 7.72 Hz, H-1'), 3.97 (m, 1 H, H-5'), 3.73 (m, 1 H, H-4'), 3.71 (m, 2 H, H-6'), 3.57 (m, 2 H, H-6), 3.55 (m, 1 H, H-5), 3.46 (m, 1 H, H-3'), 3.44 (m, 1 H, H-4), 3.42 (m, 1 H, H-3), 3.35 (m, 1 H, H-2'), 2.94 (m, 1 H, H-2), 1.86 (s, 3 H, SMe).

13C NMR (D$_2$O) δ: 103.12 (C-1'), 87.02 (C-1), 79.31 (C-4), 75.49 (C-5), 73.19 (C-3), 72.66 (C-3'), 71.28 (C-5'), 71.05 (C-2'), 68.64 (C-4'), 61.13 C-6), 60.19 (C-6), 54.81 (C-2), 12.68 (SMe).

General Procedure for the Preparation of Lactosamine and Derivatives Thereof from N-benzyloxycarbonyl Derivatives of Lactosamine:

The reaction typically carried out in solution using H$_2$ as a reductive agent. Solvents including but not limited to methanol, ethanol, water, dioxane, THF, alcohols, and the mixtures of thereof can be used for such chemical transformation. The reaction could be catalyzed with numerous Pd, Ni, Pt or other metal catalysts known in the art at a wide range of temperature and pressure. H$_2$ source can be H$_2$ gas, or other reagent like formic acid or ammonium formiate. The reaction time typically varied from 1 h to 3 d depending on the structures, the set temperature, the set pressure, and the nature of the reactive agent. The products are isolated in high yields from 80% up to 95%.

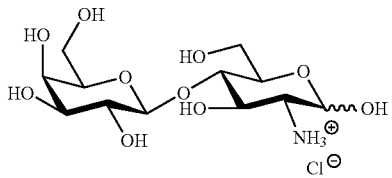

N-benzyl,N-benzyloxycarbonyl lactosamine (200 mg) was dissolved in MeOH (30 mL) and HCl in MeOH (400 μL, 1.4 mmol/mL) added to the mixture followed by addition of Pd/C (50 mg) and stirred under H$_2$ (20 bar) for 8 h. The catalyst filtered off and the filtrate concentrated affording lactosamine (100 mg) as a white powder.

MNR data: See experiment above (General preparation of salts of lactosamine and lactosamine derivatives)

General Procedure for the Preparation of NAc-Lactosamine:

Two different procedures were used to prepare the target compound.

The first method was a selective N-acetylation. The reaction carried out in solution in the presence or absence a base with an acylating agent. Solvents including but not limited to acetone, methanol, ethanol, water, dioxane, DMSO, THF, DMF, alcohols, MeCN, and the mixtures of thereof can be used for such chemical transformation. Base used for the reaction are inorganic bases (like: K$_2$CO$_3$, Na$_2$CO$_3$, NaHCO$_3$, etc) or organic bases (like pyridine, triethylamine, Hunig's base, etc.). Acylating agents are activated acetic acid derivatives known in art. Typically acetic-anhydride and acetyl chloride used as acylating agent. The temperature of the reaction varied between −10° C. up to reflux temperature of the solvents.

The reaction time typically varied from 30 min to 2 d depending on the structures, the set temperature, and the nature of the reactive agent. The products are Isolated in high yields from 80% up to 90%.

The second method was a per-acetylation followed by a de-O-acetylation. The reaction first reaction carried out in solution in the presence or absence a base with an acylating agent.

Solvents including but not limited to acetone, dioxane, DMSO, THF, DMF, alcohols, MeCN, and the mixtures of thereof can be used for such chemical transformation. Base used for the reaction are inorganic bases (like: K$_2$CO$_3$, Na$_2$CO$_3$, NaHCO$_3$, etc) or organic bases (like pyridine, triethylamine, Hunig's base, etc.). Acylating agents are activated acetic acid derivatives known in art. Typically acetic-anhydride and acetyl chloride used as acylating agent. The temperature of the reaction varied between −10° C. up to reflux temperature of the solvents. The reaction time typically varied from 30 min to 2 d depending on the structures, the set temperature, and the nature of the reactive agent. The products are isolated in high yields from 75% up to 90%. The second reaction carried out in solution in the presence of a base. Solvents including but not limited to acetone, methanol, ethanol, water, dioxane, DMSO, THF, DMF, alcohols, MeCN, and the mixtures of thereof can be used for such chemical transformation. Base used for the reaction are inorganic bases (like: K$_2$CO$_3$, Na$_2$CO$_3$, NaHCO$_3$, etc) or organic bases (like NaOMe, NaOEt, etc.). The temperature of the reaction varied between 0° C. up to reflux temperature of the solvents. The reaction time typically varied from 30 min to 1 d depending on the structures, the set temperature, and the nature of the reactive agent. The products are isolated in high yields from 70% up to 90%

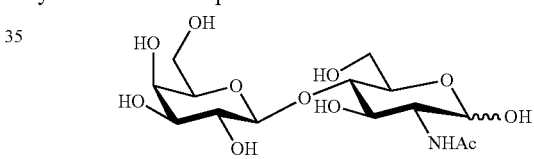

First method: Lactosamine (50 mg) dissolved in MeOH (1 mL) and the mixture cooled to 0° C. Then Ac$_2$O (100 μL) was added to the mixture and stirred at r.t. for 20 min. The product isolated by precipitation with acetone (1 mL) and hexane (1 mL) affording 30 mg white powder.

1H NMR. (D$_2$O) δ: 4.98 (d, 1 H, J$_{1,2}$ 2.00 Hz, H-1α), 4.49 (d, 1 H, J$_{1,2}$ 7.29 Hz, H-1β), 4.25 (d, 1 H, J$_{1',2'}$ 7.71 Hz, H-1'α and β), 3.68 (dd, 1 H, H-2α), 3.52 (m, 1 H, H-2β), 3.34 (m, 1 H, H-2'α and β), 1.82 (s, 3 H, NHAc).

13C NMR (D$_2$O) δ: 174.49 (CO), 102.87 (C-1'α and β), 94.90 (C-1β), 90.59 (C-1α), 78.74, 75.41, 72.53, 71.01, 70.31, 69.32 68.59, 61.10, 59.95 and 53.76 (C-2, 3, 4, 5, 6, C-2', 3', 4', 5', 6', all α).

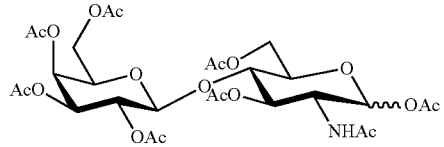

Second method: Lactosamine (1 g) dissolved in pyridine (6 mL) and Ac2O (3 mL) added to the mixture and kept for 5 h. Then the mixture concentrated and co-concentrated with toluene. The product isolated by column chromatography.

1H NMR. (CDCl$_3$) δ: 6.06 (d, 1 H, J$_{1,2}$ 3.61 Hz, H-1α), 5.96 (d, 1 H, J$_{2,NH}$ 9.77 Hz, NHβ), 5.74 (d, 1 H, J$_2$,NH 9.14

Hz, NHα), 5.61 (d, 1 H, J$_{1,2}$ 7.77 Hz, H-1β), 5.34 (m, 2 H, H-4'α and β), 5.21 (m, 2 H, H-3α and β), 5.07 (m, 2 H, H-2'α and β), 4.94 (m, 2 H, H-3'α and β), 4.51 (d, 1 H, J$_{1',2'}$ 7.87 Hz, H-1'α), 4.46 (d, 1 H, J$_{1',2'}$ 7.83 Hz, H-1'β), 4.43 and 4.11 (m, 8 H, H-6, H-6'α and β), 4.36 and 4.29 (m, 2 H, H-2α and β), 3.87 and 3.83 (m, 2 H, H-4α and β), 3.84 and 3.77 (m, 4 H, H-5, H-5'α and βp).

13C NMR (CDCl$_3$) δ: 171.34, 170.48, 170.30, 170.29, 170.28, 170.27, 170.16, 170.09, 170.04, 170.01, 169.98, 169.97, 169.38, 169.33, 169.25 and 168.76 (16×CO), 101.19 and 100.74 (C-1'α and β), 92.26 and 90.38 (C-1α and β), 75.64, 74.67, 73.32, 71.93, 70.87, 70.81, 70.66, 70.66, 70.53, 70.26, 68.97 and 68.82 (C-3, C-4, C-5, C-2', C-3', C-5'α and β), 66.51 and 66.47 (C-4'α and β), 61.47, 61.46, 60.74 and 60.69 (C-6 and C-6'α and β), 51.74 and 50.76 (C-2α and β) 23.04 and 22.95 (NAcα and β).

The per-acetylated lactosamine (250 mg) dissolved in MeOH (20 mL) and NaOMe (35 mg) added to the mixture and stirred for 5 h. The mixture neutralized with Ambertlite IR 120H$^+$, filtered and concentrated to afford NAc-lactosamine.

NMR data: See experiment before.

The invention claimed is:

1. A compound represented by Formula 1:

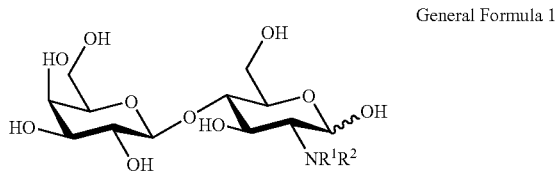

General Formula 1 wherein R$^1$ is selected from the group consisting of optionally substituted acyl and optionally substituted alkyloxy-carbonyl; and R$^2$ is selected from the group consisting of optionally substituted benzyl, optionally substituted benzhydryl, optionally substituted trityl, and optionally substituted naphthylmethyl, wherein the R$^1$ and R$^2$ groups are optionally substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms, except for when R$^1$ is defined as the optionally substituted acyl group, wherein the optionally substituted acyl group may be substituted one or several times with at least one substituent selected from the group consisting of hydroxy, C$_{1-6}$-alkoxy, C$_{2-6}$-alkenyloxy, carboxy, oxo, C$_{1-6}$-alkoxycarbonyl, C$_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di(C$_{1-6}$-alkyl)amino, carbamoyl, mono- and di(C$_{1-6}$-alkyl)aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkylcarbonylamino, cyano, guanidino, carbamido, C$_{1-6}$-alkyl-sulphonyl-amino, aryl-sulphonyl-amino, heteroaryl-sulphonyl-amino, C$_{1-6}$-alka-noyloxy, C$_{1-6}$-alkyl-sulphonyl, C$_{1-6}$-alkyl-sulphinyl, C$_{1-6}$-alkylsulphonyloxy, nitro, C$_{1-6}$-alkylthio, and halogen, wherein any alkyl or alkoxy group in the substituents for the optionally substituted acyl group may be substituted with at least one of hydroxy, C$_{1-6}$-alkoxy, C$_{2-6}$-alkenyloxy, amino, mono- and di(C$_{1-6}$-alkyl)amino, carboxy, C$_{1-6}$-alkylcarbonylamino, halogen, C$_{1-6}$-alkylthio, C$_{1-6}$-alkyl-sulphonyl-amino, and guanidino.

2. A compound represented by Formula 2:

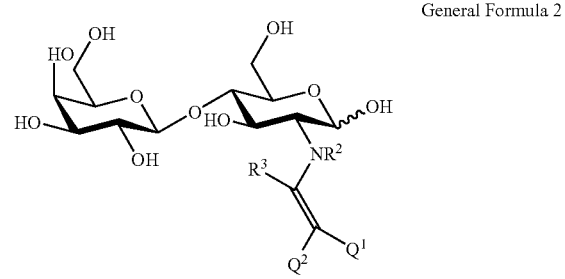

General Formula 2 wherein

R$^2$ is hydrogen or one selected from the group consisting of optionally substituted benzyl, optionally substituted benzhydryl, optionally substituted trityl, and optionally substituted naphthylmethyl;

R$^3$ is selected from the group consisting of optionally substituted C$_{1-6}$-alkyl, optionally substituted heteroalkyl, optionally substituted heterocyclyl, optionally substituted aryl, optionally substituted C$_{2-6}$-acyl, and hydrogen; and Q$^1$ and Q$^2$ are independently selected from the group consisting of electron withdrawing substituents, wherein the electron withdrawing substituents are selected from the group consisting of CN, C=OOH, C=OOR$^4$, C=OR$^4$, C=ONH$_2$, C=ONHR$^4$, C=ONR$^4$R$^5$, optionally substituted aryl, CF$_3$, CCl$_3$, SOR$^4$, SO$_2$R$^4$, and optionally substituted acyl, wherein R$^4$ and R$^5$ are at least one of optionally substituted alkyl, and optionally substituted aryl, wherein the R$^2$, R$^3$, R$^4$ and R$^5$ groups may be optionally substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms, except for when the R$^3$ group is defined as the optionally substituted C$_{1-6}$-alkyl group, the optionally substituted heteroalkyl group, or the optionally substituted C$_{2-6}$-acyl group, or the R$^4$ and R$^5$ groups are defined as the optionally substituted alkyl group, wherein the optionally substituted C$_{1-6}$-alkyl group, the optionally substituted heteroalkyl group, the optionally substituted C$_{2-6}$-acyl group or the optionally substituted alkyl group may be substituted one or several times with at least one substituent selected from the group consisting of hydroxy, C$_{1-6}$-alkoxy, C$_{2-6}$-alkenyloxy, carboxy, oxo, C$_{1-6}$-alkoxycarbonyl, C$_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di(C$_{1-6}$-alkyl)amino, carbamoyl, mono- and di(C$_{1-6}$-alkyl)aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkylcarbonylamino, cyano, guanidino, carbamido, C$_{1-6}$-alkyl-sulphonyl-amino, aryl-sulphonyl-amino, heteroaryl-sulphonyl-amino, C$_{1-6}$-alka-noyloxy, C$_{1-6}$-alkyl-sulphonyl, C$_{1-6}$-alkyl-sulphinyl, C$_{1-6}$-alkylsulphonyloxy, nitro, C$_{1-6}$-alkylthio, and halogen, wherein any alkyl or alkoxy group in the substituents for the optionally substituted $C_{1-6}$-alkyl group, the optionally substituted heteroalkyl group, or the optionally substituted $C_{2-6}$-acyl group may be substituted with at least one of hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, and guanidino.

3. The compound according to claim 2, wherein the compound is represented by Formula 8:

Formula 8

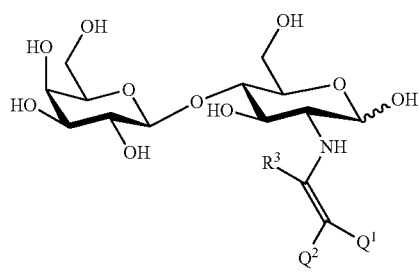

wherein
$R^3$, $Q^1$ and $Q^2$ are as defined in Formula 2.

4. The compound according to claim 2, wherein the compound is represented by Formula 3:

Formula 3

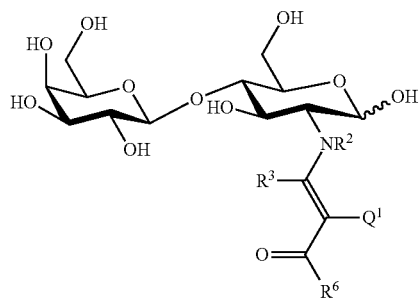

wherein
$R^2$, $R^3$ and $Q^1$ are as defined for Formula 2; and
$R^6$ is selected from the group consisting of $R^4$, OH, $OR^4$, $NH_2$, $NHR^4$, and $NHR^4R^5$, wherein $R^4$ and $R^5$ are as defined in Formula 2.

5. The compound according to claim 3, wherein the compound is represented by Formula 9:

Formula 9

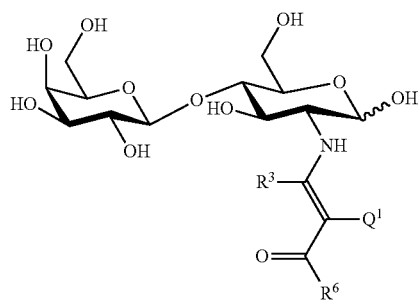

wherein $R^3$ and $Q^1$ are as defined in Formula 2, and $R^6$ is selected from the group consisting of $R^4$, OH, $OR^4$, $NH_2$, $NHR^4$, and $NHR^4R^5$, wherein $R^4$ and $R^5$ are as defined in Formula 2.

6. The compound according to claim 4, wherein the compound is represented by Formula 4:

Formula 4

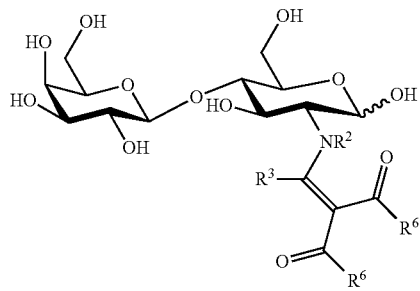

wherein $R^2$ and $R^3$ are as defined in Formula 2; and
wherein $R^6$ is as defined in Formula 3.

7. The compound according to claim 4, wherein the compound is represented by Formula 10:

Formula 10

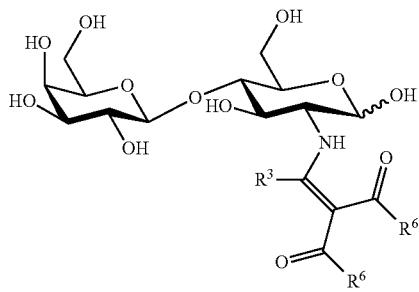

wherein
$R^3$ is as defined in Formula 2; and
$R^6$ is as defined for Formula 3.

8. A compound represented by Formula 5:

Formula 5

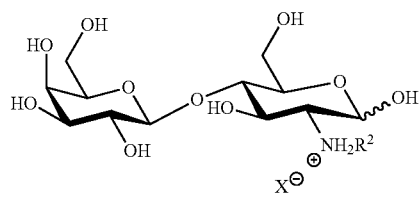

wherein
$R^2$ is hydrogen or one selected from the group consisting of optionally substituted benzyl, optionally substituted benzhydryl, optionally substituted trityl, and optionally substituted naphthylmethyl;
wherein the optionally substituted benzyl, optionally substituted benzhydryl, optionally substituted trityl, and optionally substituted naphthylmethyl groups may be substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms; and
X is any inorganic or organic anion selected from the group consisting of chloride (Cl$^-$), bromide (Br$^-$), iodide (I$^-$), acetate, lactate, maleate, fumerate, oxalate, sulphate, hydrogensulphate, nitrate, phosphate, hydrogenphosphate, and dihydrogenphosphate.

9. A compound represented by Formula 6:

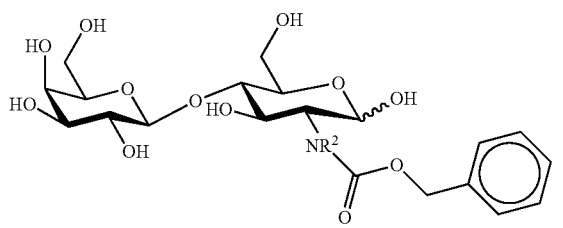

Formula 6 wherein R² is one selected from the group consisting of optionally substituted benzyl, optionally substituted benzhydryl, optionally substituted trityl, and optionally substituted naphthylmethyl, and wherein the optionally substituted benzyl, optionally substituted benzhydryl, optionally substituted trityl, and optionally substituted naphthylmethyl groups may be substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms.

10. A compound represented by Formula 7:

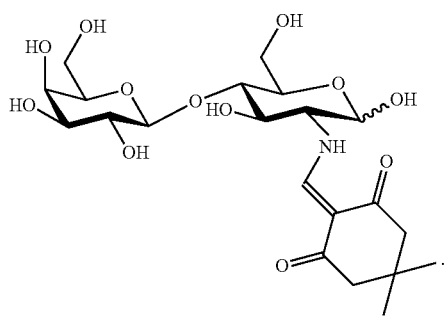

Formula 7

11. A method for the preparation of a N-substituted lactosamine derivative of Formula 1 according to claim 1, said method comprising the step of acylation, or carbamoylation of optionally substituted N-benzyl-, N-benzhydryl-, N-trityl- and N-naphthylmethyl lactosamine derivatives,

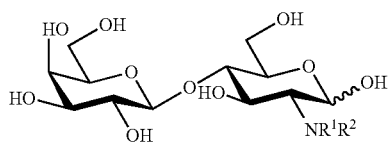

Formula 1 wherein R¹ is selected from the group consisting of optionally substituted acyl and optionally substituted alkyloxy-carbonyl; and R² is selected from the group consisting of optionally substituted benzyl, optionally substituted benzhydryl, optionally substituted trityl, and optionally substituted naphthylmethyl, wherein the R¹ and R² groups are optionally substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms, except for when R¹ is defined as the optionally substituted acyl group, wherein the optionally substituted acyl group may be substituted one or several times with at least one substituent selected from the group consisting of hydroxy, $C_{1-6}$-alkoxy, $C_{2-6}$-alkenyloxy, carboxy, oxo, $C_{1-6}$-alkoxycarbonyl, $C_{1-6}$-alkylcarbonyl, formyl, aryl, aryloxycarbonyl, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alka-noyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio, and halogen, wherein any alkyl or alkoxy group in the substituents for the optionally substituted acyl group may be substituted with at least one of hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, and guanidino.

12. A method for the preparation of acyclic vinylogous derivatives of N-substituted lactosamine derivatives of Formula 2, said method comprising the step of acyclic vinylogous amide protection of substituted/unsubstituted N-benzyl-, N-benzhydryl-, N-trityl- and N-naphthylmethyl lactosamine derivatives,

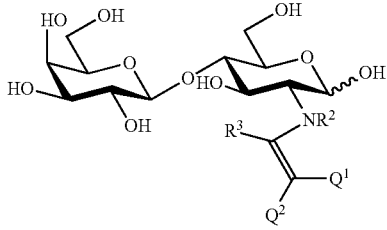

Formula 2 wherein

R² is hydrogen or one selected from the group consisting of optionally substituted benzyl, optionally substituted benzhydryl, optionally substituted trityl, and optionally substituted naphthylmethyl;

R³ is selected from the group consisting of optionally substituted $C_{1-6}$-alkyl, optionally substituted heteroalkyl, optionally substituted heterocyclyl, optionally substituted aryl, optionally substituted $C_{2-6}$-acyl, and hydrogen; and Q¹ and Q² are independently selected from the group consisting of electron withdrawing substituents, wherein the electron withdrawing substituents are selected from the group consisting of CN, C=OOH, C=OOR⁴, C=OR⁴, C=ONH₂, C=ONHR⁴, C=ONR⁴R⁵, optionally substituted aryl, CF₃, CCl₃, SOR⁴, SO₂R⁴, and optionally substituted acyl, wherein R⁴ and R⁵ are at least one of optionally substituted alkyl, and optionally substituted aryl, wherein the R², R³, R⁴ and R⁵ groups may be optionally substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms, except for when the R3 group is defined as the optionally substituted $C_{1-6}$-alkyl group, the optionally substituted heteroalkyl group, or the optionally substituted $C_{2-6}$-acyl group, or the $R^4$ and $R^5$ groups are defined as the optionally substituted alkyl group, wherein the optionally substituted $C_{1-6}$-alkyl group, the optionally substituted heteroalkyl group, the optionally substituted $C_{2-6}$-acyl group or the optionally substituted alkyl group may be substituted one or several times with at least one substituent selected from the group consisting of hydroxy, $C_{1-6}$-alkoxy, $C_{2-6}$-alkenyloxy, carboxy, oxo, $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alka-noyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio, and halogen, wherein any alkyl or alkoxy group in the substituents for the optionally substituted $C_{1-6}$-alkyl group, the optionally substituted heteroalkyl group, or the optionally substituted $C_{2-6}$-acyl group may be substituted with at least one of hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, and guanidino.

13. A method for the preparation of derivatives of N-substituted lactosamine salts of Formula 5, said method comprising:
   a. salt formation of N-substituted lactosamine derivatives corresponding to the salts of Formula 5 purified by chromatography
   b. salt formation of N-substituted lactosamine corresponding to the salts of Formula 5 as an unseparated component of Heyns re-arrangement followed by purification
   c. vinylogous amide deprotection of compounds represented by Formulae 2 followed by salt formation with acids; or
   d. N-acyl deprotection of compounds characterized by Formula 1, followed by salt formation with acids,

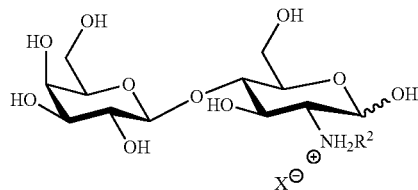

Formula 5 wherein
   $R^2$ is hydrogen or one selected from the group consisting of optionally substituted benzyl, optionally substituted benzhydryl, optionally substituted trityl, and optionally substituted naphthylmethyl;
   wherein the optionally substituted benzyl, optionally substituted benzhydryl, optionally substituted trityl, and optionally substituted naphthylmethyl groups may be substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms; and
X is any inorganic or organic anion selected from the group consisting of chloride (Cl$^-$), bromide (Br$^-$), iodide (I$^-$), acetate, lactate, maleate, fumerate, oxalate, sulphate, hydrogen sulphate, nitrate, phosphate, hydrogenphosphate, and dihydrogenphosphate;

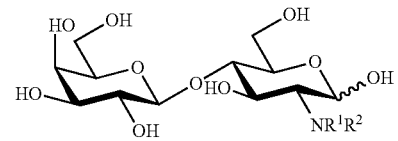

Formula 1 wherein
   $R^1$ is selected from the group consisting of optionally substituted acyl and optionally substituted alkyloxy-carbonyl; and
   $R^2$ is selected from the group consisting of optionally substituted benzyl, optionally substituted benzhydryl, optionally substituted trityl, and optionally substituted naphthylmethyl,
   the $R^1$ and $R^2$ groups are optionally substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms,
   except for when $R^1$ is defined as the optionally substituted acyl group, wherein the optionally substituted acyl group may be substituted one or several times with at least one substituent selected from the group consisting of hydroxy, $C_{1-6}$-alkoxy, $C_{2-6}$-alkenyloxy, carboxy, oxo, $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alka-noyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio, and halogen, wherein any alkyl or alkoxy group in the substituents for the optionally substituted acyl group may be substituted with at least one of hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, and guanidine;

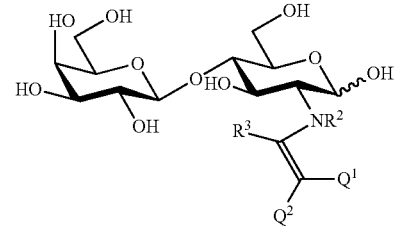

Formula 2 wherein
- R² is hydrogen or one selected from the group consisting of optionally substituted benzyl, optionally substituted benzhydryl, optionally substituted trityl, and optionally substituted naphthylmethyl;
- R³ is selected from the group consisting of optionally substituted $C_{1-6}$-alkyl, optionally substituted heteroalkyl, optionally substituted heterocyclyl, optionally substituted aryl, optionally substituted $C_{2-6}$-acyl, and hydrogen; and
- Q¹ and Q² are independently selected from the group consisting of electron withdrawing substituents,
- wherein the electron withdrawing substituents are selected from the group consisting of CN, C=OOH, C=OOR⁴, C=OR⁴, C=ONH₂, C=ONHR⁴, C=ONR⁴R⁵, optionally substituted aryl, CF₃, CCl₃, SOR⁴, SO₂R⁴, and optionally substituted acyl, wherein R⁴ and R⁵ are at least one of optionally substituted alkyl, and optionally substituted aryl,
- wherein the R², R³, R⁴ and R⁵ groups may be optionally substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms,
- except for when the R³ group is defined as the optionally substituted $C_{1-6}$-alkyl group, the optionally substituted heteroalkyl group, or the optionally substituted $C_{2-6}$-acyl group, or the R⁴ and R⁵ groups are defined as the optionally substituted alkyl group, wherein the optionally substituted $C_{1-6}$-alkyl group, the optionally substituted heteroalkyl group, the optionally substituted $C_{2-6}$-acyl group or the optionally substituted alkyl group may be substituted one or several times with at least one substituent selected from the group consisting of hydroxy, $C_{1-6}$-alkoxy, $C_{2-6}$-alkenyloxy, carboxy, oxo, $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alka-noyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio, and halogen, wherein any alkyl or alkoxy group in the substituents for the optionally substituted $C_{1-6}$-alkyl group, the optionally substituted heteroalkyl group, or the optionally substituted $C_{2-6}$-acyl group may be substituted with at least one of hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, and guanidine.

14. A method for the preparation of N-carbobenzyloxy-lactosamine derivatives represented by Formula 6, said method comprising the step of treating N-substituted lactosamine derivatives with activated benzyloxycarbonyl reagents,

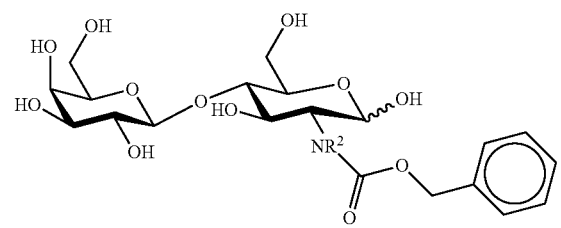

Formula 6 wherein R² is one selected from the group consisting of optionally substituted benzyl, optionally substituted benzhydryl, optionally substituted trityl, and optionally substituted naphthylmethyl, and wherein the optionally substituted benzyl, optionally substituted benzhydryl, optionally substituted trityl, and optionally substituted naphthylmethyl groups may be substituted with one substituent selected from the group consisting of halogen, nitro, amino, azido, oxo, hydroxyl, thiol, carboxy, carboxy ester, carboxamide, alkylamino, alkyldithio, alkylthio, alkoxy, acylamido, acyloxy, and acylthio, each substituent consisting of 1 to 3 carbon atoms.

15. A method for the preparation of N-Dmc-protected lactosamine derivatives of Formula 7, said method comprising the step of vinylogous amide protection of optionally substituted lactosamine derivatives,

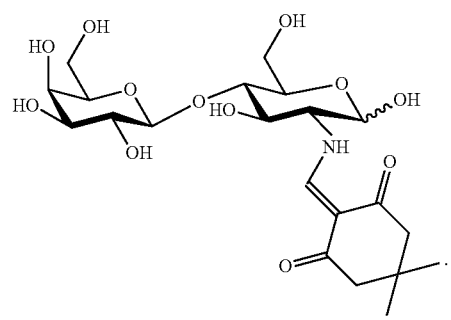

Formula 7

16. A method for the preparation of acyclic vinylogous amid derivatives of lactosamine of Formula 8, said method comprising the step of acyclic vinylogous amide protection of optionally substituted lactosamine derivatives,

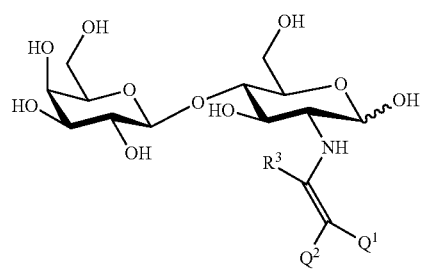

Formula 8 wherein R³, Q¹ and Q² are as defined in Formula 2 according to claim 12.

17. A method for the preparation of lactosamine, lactosamine salts and N-acetyl lactosamine, said method comprising the step of hydrogenolysis of compounds of Formula 1 according to claim 11.

18. A method for the preparation of lactosamine, lactosamine salts and N-acetyl lactosamine, said method comprising:
- hydrogenolysis of a compound represented by Formula 1 according to claim 11, and
- after the hydrogenolysis, removing acyclic vinylogous moieties and performing selective N-acetylation in the case of N-acetyllactosamine preparation; or
- removing acyclic vinylogous moieties of a compound represented by Formula 1 either by N-nuclophiles or chlorine treatment, and
- after the removing the acyclic vinylogous moieties, hydrogenolysis and selective N-acetylation in the case of N-acetyllactosamine preparation.

19. A method for the preparation of lactosamine, lactosamine salts and N-acetyl lactosamine, said method comprising:
- hydrogenolysis of benzyloxycarbamate derivative of lactosamine of Formula 6 according to claim 14; and
- after the hydrogenoloysis, selective N-acetylation in the case of N-acetyllactosamine preparation.

20. A method for the preparation of lactosamine, lactosamine salts and N-acetyl lactosamine, said method comprising:
- Dmc deprotection of Dmc-protected lactosamine of Formula 7 according to claim 15 using one of ammonia, primary amines, hydrazines, hydroxylamine derivatives, basic ion exchange resin and chlorine gas; and
- after the Dmc deprotection, selective N-acetylation in the case of N-acetyllactosamine preparation.

21. A method for the preparation of lactosamine, lactosamine salts and N-acetyl lactosamine, said method comprising:
- acyclic vinylogous amide deprotection of lactosamine derivatives of Formula 8 according to claim 16 using one of ammonia, primary amines, hydrazines, hydroxylamine derivatives, basic ion exchange resin and chlorine gas; and
- after the acyclic vinylogous amide deprotection, selective N-acetylation in the case of N-acetyllactosamine preparation.

* * * * *